US012753194B2

(12) United States Patent
Belova-Magri et al.

(10) Patent No.: US 12,753,194 B2
(45) **Date of Patent: *Oct. 6, 2026**

(54) TRIAZINE SILANE COMPOUND AND ITS USAGE AS ADHESION PROMOTOR

(71) Applicant: Atotech Deutschland GmbH & Co. KG, Berlin (DE)

(72) Inventors: Valentina Belova-Magri, Berlin (DE); Stefanie Ackermann, Berlin (DE); Philipp Haarmann, Berlin (DE); Martin Thoms, Berlin (DE); Norbert Lützow, Berlin (DE); Jan Knaup, Berlin (DE); Tatjana Königsmann, Berlin (DE); Bernd Froese, Berlin (DE)

(73) Assignee: Atotech Deutschland GmbH & Co. KG, Berlin (DE)

( * ) Notice: Subject to any disclaimer, the term of this patent is extended or adjusted under 35 U.S.C. 154(b) by 499 days.

This patent is subject to a terminal disclaimer.

(21) Appl. No.: 18/550,148

(22) PCT Filed: Mar. 11, 2022

(86) PCT No.: PCT/EP2022/056367

§ 371 (c)(1),
(2) Date: Sep. 12, 2023

(87) PCT Pub. No.: WO2022/189646

PCT Pub. Date: Sep. 15, 2022

(65) Prior Publication Data

US 2024/0247009 A1 Jul. 25, 2024

(30) Foreign Application Priority Data

Mar. 12, 2021 (EP) .................................... 21162411

(51) Int. Cl.

| | |
|---|---|
| ***C07D 251/54*** | (2006.01) |
| ***B05D 1/18*** | (2006.01) |
| ***B05D 3/10*** | (2006.01) |
| ***B05D 5/10*** | (2006.01) |
| ***C07F 7/18*** | (2006.01) |
| ***C09D 183/08*** | (2006.01) |
| *C08G 77/26* | (2006.01) |

(52) U.S. Cl.
CPC .............. *C07F 7/1804* (2013.01); *B05D 1/18* (2013.01); *B05D 3/102* (2013.01); *B05D 5/10* (2013.01); *C07D 251/54* (2013.01); *C09D 183/08* (2013.01); *C08G 77/26* (2013.01); *C09J 2400/228* (2013.01)

(58) Field of Classification Search
CPC .. C07D 251/26; C07D 251/38; C07D 251/40; C07D 251/42; C07D 251/48; C07D 251/54; C07F 7/0812; C07F 7/0814; C07F 7/18; C07F 7/1804
See application file for complete search history.

(56) References Cited

U.S. PATENT DOCUMENTS

| | | | | |
|---|---|---|---|---|
| 4,876,344 | A | 10/1989 | Itoh et al. | |
| 11,014,946 | B2 | 5/2021 | Yamaji et al. | |
| 2001/0056139 | A1 | 12/2001 | Krafczyk | |
| 2016/0368935 | A1 | 12/2016 | Miura et al. | |
| 2022/0017755 | A1 | 1/2022 | Morikawa et al. | |
| 2024/0179851 | A1 * | 5/2024 | Belova-Magri ........ | H05K 3/227 |

FOREIGN PATENT DOCUMENTS

| | | | |
|---|---|---|---|
| CN | 102952158 | A | 3/2013 |
| CN | 105556004 | A | 5/2016 |
| CN | 107190254 | A | 9/2017 |
| CN | 111961075 | A | 11/2020 |
| EP | 339262 | A * | 11/1989 |
| JP | H06279461 | A | 10/1994 |
| JP | 2007131556 | A | 5/2007 |
| JP | 2007131580 | A | 5/2007 |
| JP | 2014240522 | A | 12/2014 |
| JP | 2015092020 | A | 5/2015 |
| JP | 2017048467 | A | 3/2017 |
| JP | 2018016865 | A | 2/2018 |
| JP | 6370836 | B2 | 7/2018 |
| JP | 6392273 | B2 | 8/2018 |
| JP | 6436819 | B2 | 11/2018 |
| WO | 2007073756 | A1 | 7/2007 |
| WO | 2019243180 | A1 | 12/2019 |
| WO | 2020148308 | A1 | 7/2020 |
| WO | 2020178146 | A1 | 9/2020 |

OTHER PUBLICATIONS

PCT/EP2022/056367; International Search Report and Written Opinion of the International Searching Authority dated Apr. 6, 2022.
Chem. Eur. J. 2009, vol. 15, Issue 25, pp. 6279-6288 (Abstract).
Mori K, "One-step preparation of functional triazinedithiols", JP2007131556A, vol. 0646, Jan. 1, 2007, pp. 1-1.
PCT/EP2022/056360; International Search Report and Written Opinion of the International Searching Authority dated Jun. 23, 2022.

* cited by examiner

*Primary Examiner* — Marc S Zimmer
(74) *Attorney, Agent, or Firm* — Renner, Otto, Boisselle & Sklar, LLP

(57) ABSTRACT

The present invention relates to a specific triazine silane compound, an oligomer thereof, a mixture comprising said compound and/or said oligomer, as well as a respective storage and working solution. Furthermore, the present invention relates to a synthesis method for said specific triazine silane compound, and the use of said working solution as a surface treatment solution.

12 Claims, 1 Drawing Sheet

Figure 1: Halo microscope imaging
| | No silane | Silane (VIa) |
|---|---|---|
| Without step (i-c) | Comparative sample C1 with GL102 without alkaline solution 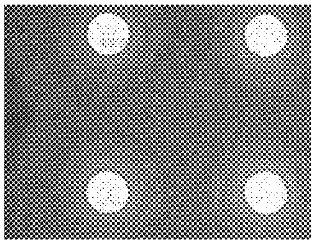 | Sample 10 with GL102 without alkaline solution 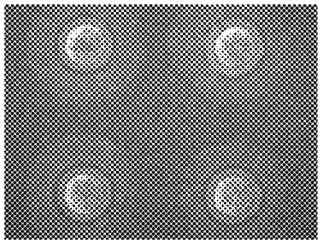 |
| With step (i-c) [300 s] | Comparative sample C1 with GL102 with alkaline solution 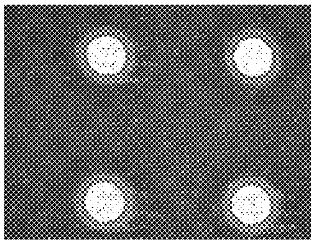 | Sample 10 with GL102 with alkaline solution 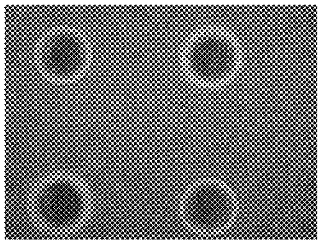 |
Figure 2: Example of halo measurement
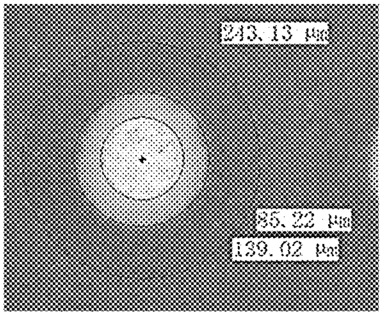

TRIAZINE SILANE COMPOUND AND ITS USAGE AS ADHESION PROMOTOR

This application is a national phase of International Application No. PCT/EP2022/056367, filed 11 Mar. 2022, which claims priority to European Patent Application No. 21162411.9, filed 12 Mar. 2021, each of which is hereby incorporated herein by reference in its entirety.

FIELD OF THE INVENTION

The present invention relates to a specific triazine silane compound, an oligomer thereof, a mixture comprising said compound and/or said oligomer, as well as a respective storage and working solution. Furthermore, the present invention relates to a synthesis method for said specific triazine silane compound, and the use of said working solution as a surface treatment solution.

Furthermore, the present invention relates to a method for increasing adhesion strength between a surface of a metal, a metal alloy or a metal oxide and a surface of an organic material comprising as a main step contacting of at least one section of said metal, metal alloy or metal oxide with a specific triazine silane compound, a specific triazine silane oligomer, or a mixture comprising said compound and/or said oligomer. Furthermore, the present invention relates to a use of said specific triazine silane compound, said specific triazine silane oligomer, or said mixture in a method for increasing adhesion strength and wedge void reduction between a surface of a metal, a metal alloy or a metal oxide and a surface of an organic material. The wedge voids, also seen in a form of halo, typically form at the interface between substrate and laminate after desmear process of structured samples.

BACKGROUND OF THE INVENTION

Heteroaromatic silane compounds are frequently utilized in the manufacturing of electronic components, in particular in surface treatment solutions, e.g. for the treatment of metal surfaces and surfaces of organic materials as a preparation for further processing steps. US 2016/0368935 A1 relates to an azole silane compound, and a surface treatment solution using the azole silane compound, a surface treatment method and use thereof. JP 2018016865 A discloses a triazole surface treatment agent containing a silane compound.

The article "Corrosion protection of copper with 3-glycidoxypropyltrimethoxysilane-based sol-gel coating through 3-amino-5-mercapto-1,2,4-triazole doping", Journal of Research on Chemical Intermediates, Volume 42, Issue 2, pages 1315 to 1328, 2015, discloses a study about corrosion protection of copper in a neutral medium by the formation of a sol-gel coating over the copper surface. It discloses that a 3-amino-5-mercapto-1,2,4-triazole-doped 3-glydidoxypropyltrimethoxysilane-based sol-gel coating on copper forms a thiolate bond to copper.

JPH 06279461 A refers to a surface treating agent for improving rust prevention on a metal surface, particularly a surface treating agent for copper foils used for copper clad laminate boards for printed circuits. The agent is an azole silane obtained by reacting 1H-1,2,4-triazole-3-thiol with 3-glycidoxypropyltrimethoxysilane at 80-200° C.

The article "Recovery of rhodium-containing catalysts by silica-based chelating ion exchangers containing N and S donor atoms", Journal of Inorganica Chimica Acta 315 (2001), pages 183 to 190 discloses 4-amino-3-methyl-1,2,4-triazole-5-thione attached to the bifunctional spacer (3-glycidoxypropyl)trimethoxysilane prior to immobilization on silica.

WO2019/243180 discloses azole silane compounds, the synthesis thereof as well as respective solution and the use in surface treatment.

WO2020/178146 discloses the use of azole silane compounds in a method for increasing adhesion strength between a surface of a metal, a metal alloy or a metal oxide and a surface of an organic material.

JP2016169300A (JP6436819B2) discloses 2,4-Diamine-substituted triazines which do not comprise silicon.

2,4,6-Triamine-substituted triazines are disclosed in Chem. Eur. J. 2009, 15, 6279-6288 and JP 2017002402 A (JP6370836B2). The use thereof in epoxy resins is disclosed in JP6392273.

Due to the structural diversity of triazine silane compounds, the majority of such compounds needs to be manufactured upon request and is typically not readily available as a standard commercial product. Thus, simple and efficient synthesis methods are demanded.

Typically, triazine silane compounds easily polymerize in the presence of water by forming silicon-oxygen-silicon bonds. This is in many cases not desired right after the synthesis of the compound. Although a polymerization might be desired for a final application, usually there is a demand to solubilize freshly synthesized compounds in a solvent such that on the one hand too much and/or too early polymerization of the monomer is prevented but on the other hand allows further processing of the compounds. Furthermore, it is desired to have a sufficiently high concentration of the respective triazine silane compound in such a solvent in order to economically ship them to another manufacturing site. As a matter of fact, solubility of known triazine silane compounds in typically utilized/desired solvents is often not sufficient.

In addition, in many cases the synthesis of heteroaromatic silane compounds includes educts comprising halides such as chloride, bromide, and iodide. During the synthesis such halides are often released, contaminating the resulting synthesis product. This typically means that in additional purification steps halides and their respective salts need to be removed. However, such additional steps significantly increase the risk of water contamination leading to premature polymerization. Furthermore, such purification steps often negatively affect the over-all yield of the final heteroaromatic silane compounds. If tolerable, such compounds are not purified and as a result halides and their respective salts remain together with the heteroaromatic silane compounds. However, in many applications it is not desired to work at all with a heteroaromatic silane compound accompanied by halides. In other cases it is not desired to utilize heteroaromatic silane compounds accompanied by an undefined amount of halides, although halides are generally accepted.

Adhesion strength is related to the physical and chemical strength by which the adhesion layer is bound to the metallic substrate.

Another aspect related to adhesion strength is the avoidance of wedge void formation. This means that during the typical follow-up steps such as lamination and curing, lasering, desmearing and reducing, wedge-like structures are formed at the interface between substrate and laminate. These so-called wedge voids are unwanted since they facilitate the peel off of the laminate. The wedge voids are often already seen as halo around the drilled hole indicating the chemical propagation to the substrate.

OBJECTIVE OF THE PRESENT INVENTION

It was therefore the first objective of the present invention, based on the above mentioned problems, to provide a triazine silane compound with increased solubility in suitable solvents. It was the second objective of the present invention to provide a synthesis method that is simple and efficient, and, above all, does not release halides and respective salts thereof such that additional purifications steps can be avoided.

It was an additional task to provide a method which does not exhibit the disadvantages regarding adhesion strength and wedge void and halo formation as described above.

DESCRIPTION OF THE INVENTION

Above mentioned first objective is solved by a triazine silane compound of formula (I)

wherein (I)

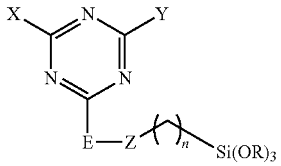

X and Y are independently selected from the group consisting of $NH_2$, $NH(NH_2)$, $NH(CH_2)_oNH_2$, SH, $SCH_3$, and $OCH_3$;

E is selected from the group consisting of —S— and —NH—$(CH_2)_m$—NH—;

Z is selected from the group consisting of

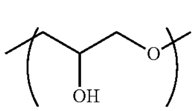

and

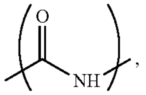

, m is an integer in the range from 2 to 12, n is an integer in the range from 1 to 12, o is an integer in the range from 2 to 12, R independently denotes ($CH_2$—$CH_2$—O)$_p$—T, wherein independently p is 0, 1, 2, 3, or 4, and T denotes H or C1 to C5 alkyl.

The second objective is solved by a synthesis method for a triazine silane compound of formula (II)

(II)

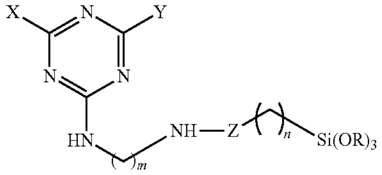

wherein

X and Y are independently selected from the group consisting of $NH_2$, $NH(NH_2)$, $NH(CH_2)_0NH_2$, SH, $SCH_3$, and $OCH_3$;

Z is selected from the group consisting of

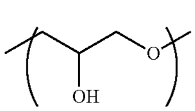

and

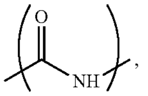

, m is an integer in the range from 2 to 12, n is an integer in the range from 1 to 12, o is an integer in the range from 2 to 12, R independently denotes ($CH_2$—$CH_2$—O)$_p$—T, wherein independently p is 0, 1, 2, 3, or 4, and T denotes H or C1 to C5 alkyl.

The synthesis method comprising the steps of (i) providing a compound of formula (III)

(III)

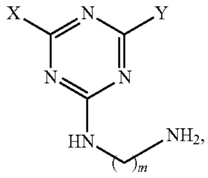

wherein X and Y are independently selected from the group consisting of $NH_2$, $NH(NH_2)$, $NH(CH_2)_oNH_2$, SH, $SCH_3$, and $OCH_3$; and m is an integer in the range from 2 to 12, o is an integer in the range from 2 to 12, (ii) providing a silane compound selected from the group of (ii-a) a silane compound of formula (IV)

(IV)

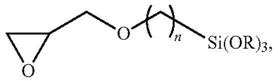

and (ii-b) a silane compound of formula (V)

$$OCN—(CH_2)_n—Si(OR)_3, \quad (V)$$

wherein in formula (IV) or (V)

R denotes ($CH_2$—$CH_2$—O)$_p$—T, wherein independently p is 0, 1, 2, 3, or 4, and T denotes C1 to C5 alkyl, and n is an integer in the range from 1 to 12, (iii) reacting in a solvent said intermediate of formula (III) with said silane compound such that above defined compound of formula (II) results, and (iv) optionally hydrolyzing the compound of formula (II) obtained in step (iii) such that at least one of R is ($CH_2$—$CH_2$—O)$_m$—Z with m=zero and Z=H.

Own experiments have shown that above mentioned synthesis method leads to triazine silane compounds with improved solubility and stability in specific solvents. Furthermore, above synthesis method utilizes educts that are free of halogen atoms. Thus, no halide ions are released during the synthesis into the respective solvent. This is very much desired because even if halide ions are required in further applications, the specific amount of respective halides can be added such that its total concentration is precisely known.

The present invention in particular refers to a specific triazine silane compound as defined above. In many cases a triazine silane compound of the present invention is preferred, wherein Y denotes NH and $N(NH_2)$, preferably NH. In other cases a triazine silane compound of the present invention is preferred, wherein Y denotes S. Among both, a Y comprising a nitrogen is preferred compared to a Y being S.

A triazine silane compound of the present invention is preferred, wherein X denotes $NH_2$, $NH(NH_2)$, $NH(CH_2)_o NH_2$, SH, $SCH_3$, or $OCH_3$, wherein o is an integer in the range from 2 to 12; preferably $NH_2$, $NH(NH_2)$, $NH(CH_2)_o NH_2$, SH, or $SCH_3$, wherein o is an integer in the range from 2 to 12; more preferably $NH_2$.

Very preferred is a triazine silane compound of the present invention, being a compound of formula (VI)

(VI)

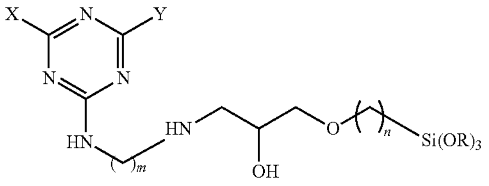

wherein
m is an integer in the range from 2 to 10,
n is an integer in the range from 1 to 10,
o is an integer in the range from 2 to 12,
R independently denotes $(CH_2—CH_2—O)_p—T$, wherein independently
p is 0, 1, 2, 3, or 4, and
T denotes H or C1 to C5 alkyl.

Particularly preferred are compounds of formula (VIa) and (VIb).

In the alternative, very preferred is a triazine silane compound of the present invention, being a compound of formula (VII)

(VII)

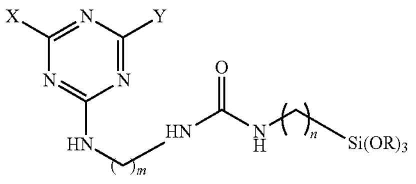

wherein
m is an integer in the range from 2 to 10,
n is an integer in the range from 1 to 10,
R independently denotes $(CH_2—CH_2—O)_p—T$, wherein independently
p is 0, 1, 2, 3, or 4, and
T denotes H or C1 to C5 alkyl.

Particularly preferred is a compound of formula (VIIa).

(VIIa)

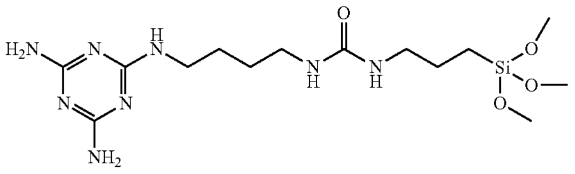

In the context of the present invention the term "independently being" (or similar expressions) in combination with a certain variable denotes that a selected feature for such a variable in a first compound is independent from a selected feature of the same variable in a second compound and, if one compound contains the same variable at least twice, it is independently selected from each other, and thus can be different. This principle likewise applies to other "independently" terms.

The present invention also refers to oligomers of the triazine silane compounds of the present invention. Thus, (VIa)

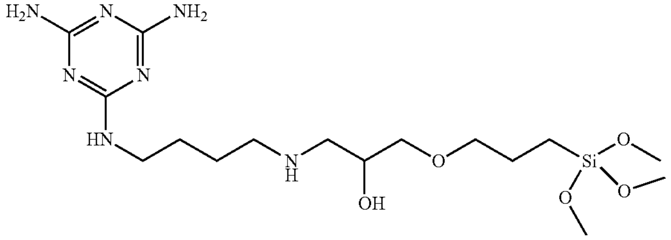

(VIb)

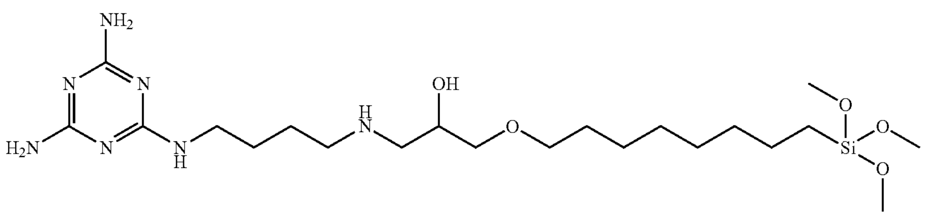

this invention refers to a triazine silane oligomer obtained by reacting in the presence of water triazine silane compounds according to formula (II)

wherein (II)

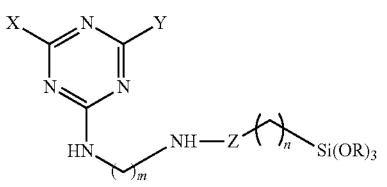

X and Y are independently selected from the group consisting of $NH_2$, $NH(NH_2)$, $NH(CH_2)_oNH_2$, SH, $SCH_3$, and $OCH_3$;

Z is selected from the group consisting of

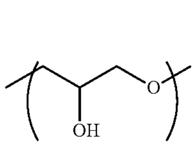 and 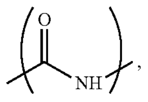, m is an integer in the range from 2 to 12, n is an integer in the range from 1 to 12, o is an integer in the range from 2 to 12, R independently denotes $(CH_2—CH_2—O)_p—T$, wherein independently p is 0, 1, 2, 3, or 4, and T denotes H or C1 to C5 alkyl (preferably compounds of formula (II) as described throughout the present text as being in particular preferred) with each other such that the triazine silane oligomer comprises at least one silicon-oxygen-silicon moiety. This reaction can be also called oligomerization.

Above mentioned oligomerization requires at least a little amount of water for hydrolysis in order to form at least some OH groups at various silicon atoms. Preferably, the triazine silane oligomer is obtained by reacting said triazine silane compounds with each other in the presence of at least 2 wt.-% of water, based on the total weight of a respective reaction composition.

In the context of the present invention, the term "triazine silane oligomer" includes the combination of at least two monomers, i.e. the reaction of at least two triazine silane compounds of the present invention with each other. Furthermore, this term includes three, four, five, six, seven, eight, nine, ten, eleven and up to twelve monomers. Preferred is a triazine silane oligomer of the present invention, wherein the oligomer is selected from the group consisting of a triazine silane dimer, an triazine silane trimer, an triazine silane tetramer, an triazine silane pentamer, an triazine silane hexamer, an triazine silane heptamer, and an triazine silane octamer. More preferred is a triazine silane oligomer of the present invention, wherein the oligomer is selected from the group consisting of a triazine silane dimer, a triazine silane trimer, and a triazine silane tetramer. The latter alternatively means that a triazine silane oligomer of the present invention is preferred, wherein the oligomer comprises one, two, or three silicon-oxygen-silicon moieties, respectively.

On the basis of the triazine silane compound of the present invention a huge variety of oligomers of the present invention can be formed. Thus, the oligomers of the present invention are best and fittingly described by their reacting with each other.

In the context of the present invention, the term "at least" in combination with a particular value denotes (and is exchangeable with) this value or more than this value. For example, above mentioned "at least one silicon-oxygen-silicon moiety" denotes (and is exchangea-ble with) "one or more than one silicon-oxygen-silicon moiety". Most preferably, "at least one" denotes (and is exchangeable with) "one, two, three or more than three".

Most preferred is an oligomer of the present invention, wherein the oligomer is a compound of formula (VIII)

(VIII)

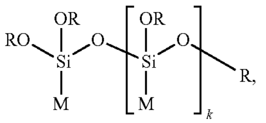

wherein

R independently denotes $(CH_2—CH_2—O)_p—T$, wherein p is 0, 1, 2, 3, or 4, preferably 0, 1, or 2, and T denotes H or C1 to C5 alkyl, k is 1, 2 or 3, preferably 1 or 2, and M independently denotes a moiety of formula (II-I)

(II-I)

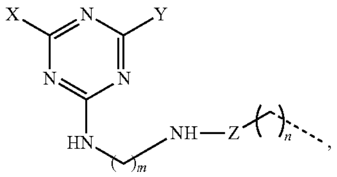

wherein in formula (II-I)

X and Y are independently selected from the group consisting of $NH_2$, $NH(NH_2)$, $NH(CH_2)_oNH_2$, SH, $SCH_3$, and $OCH_3$, preferably $NH_2$;

Z is selected from the group consisting of

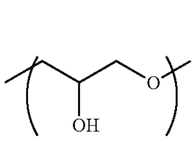 and 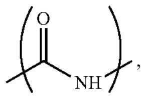, m is an integer in the range from 2 to 12, preferably in the range from 2 to 8, more preferably in the range from 2 to 6, even more preferably in the range from 3 to 4, most preferably n is 3 n is an integer in the range from 1 to 12, preferably in the range from 1 to 8, more preferably in the range from 2 to 6, even more preferably in the range from 3 to 4, most preferably n is 3, o is an integer in the range from 2 to 12.

In above moiety of formula (VIa) the dashed line denotes the covalent bond connecting the whole moiety with a silicon atom depicted in formula (VIII).

Only in a few cases a triazine silane oligomer of the present invention is even preferred, wherein k is an integer in the range from 1 to 7, preferably in the range from 1 to 5. However, most preferably k is 1, 2 or 3, preferably 1 or 2.

Preferably, the oligomer of the present invention is a homooligomer. This means that preferably identical monomers are combined with each to form the oligomer.

Alternatively preferred is that in an oligomer of the present invention at least all those moieties not forming the silicon-oxygen-silicon backbone (i.e. the triazine moieties and the ether moieties which are linking the triazine moieties to the silicon atom) are identical in their chemical formulas. In such a case, M preferably is not independently defined.

The triazine silane compound of the present invention and the triazine silane oligomer of the present invention can be present as a mixture. Alternatively, more than one compound or more than one oligomer can be present as a mixture. Typically, an organic solvent facilitates solubility. Thus, the present invention also refers to a mixture comprising, preferably consisting of, (a) one or more than one triazine silane compound according to the present invention (as described throughout the present text, preferably as described as being preferred), and/or
one or more than one triazine silane oligomer according to the present invention (as described throughout the present text, preferably as described as being preferred),
(b) one or more than one organic solvent.

Preferably the mixture of the present invention is substantially free of, preferably does not comprise, halide ions.

In the context of the present invention, the term "substantially free" of a subject-matter (e.g. a compound, a material, etc.) denotes that said subject-matter is not present at all or is present only in (to) a very little and undisturbing amount (extent) without affecting the intended purpose of the invention. For example, such a subject-matter might be added or utilized unintentionally, e.g. as unavoidable impurity. "Substantially free" preferably denotes 0 (zero) ppm to 50 ppm, based on the total weight of the mixture (if defined for said mixture), preferably 0 ppm to 25 ppm, more preferably 0 ppm to 10 ppm, even more preferably 0 ppm to 5 ppm, most preferably 0 ppm to 1 ppm. Zero ppm denotes that a respective subject-matter is not comprised at all, which is most preferred. This principle applies likewise to other aspects of the present invention, e.g. the storage solution of the present invention (see text below) and the working solution of the present invention (see also text below).

Preferred is a mixture of the present invention, wherein in said mixture the total amount of all triazine silane compounds of the present invention and oligomers of the present invention together is in the range from 5 wt.-% to 30 wt.-%, based on the total weight of said mixture, preferably is in the range from 8 wt.-% to 28 wt.-%, more preferably is in the range from 12 wt.-% to 26 wt.-%, even more preferably is in the range from 15 wt.-% to 24 wt.-%, most preferably is in the range from 17 wt.-% to 22 wt.-%. Preferably the mixture is substantially free of, preferably does not comprise, any other triazine silane compounds and triazine silane oligomers, respectively, not being according to the present invention.

Very preferred is a mixture of the present invention, wherein said mixture is substantially free of, preferably does not comprise, water. Thus, preferred is a mixture of the present invention, wherein the one or more than one triazine silane compound according to the present invention is substantially free of, preferably does not comprise, —SiOH groups.

Preferred is a mixture of the present invention, wherein the one or more than one organic solvent comprises a solvent selected from the group consisting of acetone, 1,3-dioxolane, acetonitrile, 1,4-dioxane, methanol, ethanol, 1-propanol, 2-propanol, t-butanol, prop-2-en-1-ol, ethyl lactate, ethylene glycol monomethyl ether acetate, N,N-dimethylformamide, 2-butoxyethanol, di(propylene glycol) methyl ether, tetrahydrofurfuryl alcohol, N-methyl-2-pyrrolidone, 2-(2-methoxyethoxy)ethanol, gamma-butyrolactone, ethylene glycol, propylene glycol, dipropylene glycol, epsilon-caprolactone, diethylene glycol monobutyl ether, ethylene glycol monobutyl ether, tetrahydrothiophene-1-oxide, diethylene glycol monobutyl ether acetate, propylene carbonate, sulfolane, glycerol, and mixtures thereof.

Very preferred is a mixture of the present invention, wherein the one or more than one organic solvent comprises a solvent selected from the group consisting of methanol, ethanol, 1-propanol, 2-propanol, t-butanol, di(propylene glycol) methyl ether, ethylene glycol, propylene glycol, dipropylene glycol, diethylene glycol monobutyl ether, ethylene glycol monobutyl ether, and mixtures thereof.

In a few cases very preferred is a mixture of the present invention, wherein the one or more than one organic solvent comprises a solvent selected from the group consisting of glycol ethers, preferably selected from the group consisting of di(propylene glycol) methyl ether, diethylene glycol monobutyl ether, ethylene glycol monobutyl ether, and mixtures thereof.

In the context of the present invention, above defined mixture of the present invention is preferably a direct result of a respective synthesis procedure such as the synthesis method of the present invention (for more details see below).

Furthermore, preferred is a mixture according to the present invention (as described throughout the present text, preferably as described as being preferred), wherein all triazine silane compounds according to the present invention (as described throughout the present text, preferably as described as being preferred) and all triazine silane oligomers according to the present invention (as described throughout the present text, preferably as described as being preferred) represent at least 51 mol-% of all compounds comprising at least one silicon atom in said mixture, preferably represent at least 60 mol-%, more preferably represent at least 70 mol-%, most preferably represent at least 80 mol-%, even most preferably represent at least 90 mol-%. The aforementioned preferably applies likewise to the storage solution of the present invention (see text below) and the working solution of the present invention (see text below), respectively.

The present invention also refers to a storage solution comprising (a) one or more than one triazine silane compound according to the present invention (as described throughout the present text, preferably as described as being preferred), and
optionally one or more than one triazine silane oligomer according to the present invention (as described throughout the present text, preferably as described as being preferred),
(b) optionally water,
(c) one or more than one water miscible organic solvent, with the proviso that, if water is present, the pH is 9 or higher.

Preferably the storage solution of the present invention is substantially free of, preferably does not comprise, halide ions. Only in a few cases it is preferred that halide ions are present by intentionally adding halide ions, preferably by intentionally adding chloride ions.

Preferred is a storage solution of the present invention, wherein in the solution the total amount of all triazine silane compounds according to the present invention (as described throughout the present text, preferably as described as being preferred) and all triazine silane oligomers according to the present invention (as described throughout the present text, preferably as described as being preferred) together is in the range from 0.2 wt.-% to 30 wt.-%, based on the total weight of the storage solution, preferably is in the range from 0.5 wt.-%, to 28 wt.-%, more preferably is in the range from 0.7 wt.-%, to 25 wt.-%, even more preferably is in the range from 0.8 wt.-%, to 22 wt.-%, most preferably is in the range from 0.9 wt.-%, to 20 wt.-%.

Above described storage solution optionally contains water. Preferred is a storage solution of the present invention, wherein in the storage solution is alkaline and water is present in a total amount in the range from 10 wt.-%, to 80 wt.-%, based on the total weight of the storage solution, preferably in the range from 15 wt.-%, to 78 wt.-%, more preferably in the range from 20 wt.-%, to 76 wt.-%, even more preferably in the range from 33 wt.-%, to 74 wt.-%, most preferably in the range from 38.6 wt.-%, to 70 wt.-%.

The storage solution contains one or more than one water miscible organic solvent. Such an organic solvent facilitates the needed solubility of the respective triazine silane compounds and its oligomers, particular if they are present at comparatively higher concentrations (e.g. up to and around 15 wt.-%, see text above). Thus, preferred is a storage solution of the present invention, wherein in said solution the one or more than one water miscible organic solvent is present in a total amount in the range from 5 wt.-%, to 89.5 wt.-%, based on the total weight of the storage solution, preferably in the range from 10 wt.-%, to 84.2 wt.-%, more preferably in the range from 14 wt.-%, to 79 wt.-%, even more preferably in the range from 18 wt.-%, to 65.5 wt.-%, most preferably in the range from 24 wt.-%, to 59 wt.-%.

In many cases a storage solution of the present invention is preferred, wherein the total weight of water is lower than the total weight of all water miscible organic solvents.

As mentioned above, said storage solution is alkaline, if water is present. In the context of the present invention this means that the pH is 9 or higher. Preferred is a storage solution of the present invention, wherein the solution has a pH of 9.6 or more, preferably the pH is in the range from 10.5 to 14, more preferably the pH is in the range from 11 to 14, most preferably the pH is in the range from 12 to 14. If the pH is significantly below pH 9 the solubility of the triazine silane compounds and its oligomers is reduced, even up to the point of undesired precipitation. An acidic pH is not suitable for storage purposes because at such a pH precipitation has been observed in many cases with comparatively high concentrations of silane triazine compounds of the present invention and its corresponding oligomers. It is known from WO2019/243180 that for azole silanes, if the pH is significantly above 13, an undesired phase separation and degradation of the azole silane compounds is frequently observed. In contrast, the instant triazine silanes solutions exhibit a good phase stability at high pH values.

In addition, the instant triazine silanes solutions exhibit a good stability, i.e. no phase separation and no degradation, in a broad temperature window. In particular, such solutions are stable from −5° C. to 50° C.

In the context of the present invention, the pH is referenced to a temperature of 25° C. In an alkaline storage solution of the present invention, the alkaline pH is obtained by preferably utilizing at least one alkaline hydroxide, most preferably by utilizing sodium hydroxide.

An alkaline pH does not only allow comparatively high concentrations of said triazine silane compounds and its oligomers, respectively, in the storage solution. It furthermore strongly maintains the triazine silane compounds of the present invention in its monomeric state and significantly reduces the formation of triazine silane oligomers of the present invention. However, if such an oligomer is formed in the alkaline storage solution of the present invention, it is typically quickly hydrolyzed to form its monomeric forms due to the alkaline pH. In the storage solution of the present invention this is desired.

Preferred is a storage solution of the present invention, wherein in said solution the total weight of all triazine silane compounds according to the present invention is higher than the total weight of all triazine silane oligomers according to the present invention.

In some cases a storage solution of the present invention is preferred, wherein for at least 80 wt.-%, of the total weight of all triazine silane compounds according to the present invention Z is H and p is zero, preferably for at least 90 wt.-%, most preferably for at least 95 wt.-%. This means that in the storage solution the triazine silane compound is mostly present in its hydrolyzed form comprising SiOH-groups.

Above mentioned storage solution is in particular suitable in order to transport and/or storage the one or more than one triazine silane compound of the present invention. However, in order to utilize said compounds, for example as a surface treatment solution in the production of electronic parts, a respective working solution is preferred. Thus, the present invention further relates to a working solution having a pH in the range from 2 to 14, the solution comprising (a) one or more than one triazine silane compound according to the present invention (as described throughout the present text, preferably as described as being preferred), and/or
   one or more than one triazine silane oligomer according to the present invention (as described throughout the present text, preferably as described as being preferred),
(b) optionally, water,
(c) one or more than one water miscible organic solvent, wherein in said working solution the total amount of all triazine silane compounds according to the present invention (as described throughout the present text, preferably as described as being preferred) and all triazine silane oligomers according to the present invention (as described throughout the present text, preferably as described as being preferred) together is 10 wt.-%, or less, based on the total weight of the working solution.

In particular preferred is a working solution of the present invention with the proviso that said working solution comprises at least one triazine silane oligomer according to the present invention (as described throughout the present text, preferably as described as being preferred). This is in particular preferred for freshly prepared working solutions.

Above term "10 wt.-%, or less" does not include zero wt.-%. This means that said total amount is always >0 wt.-%, preferably at least 0.1 wt.-%.

Preferred is a working solution of the present invention, wherein in said working solution the total amount of all triazine silane compounds according to the present invention (as described throughout the present text, preferably as described as being preferred) and all triazine silane oligomers according to the present invention (as described throughout the present text, preferably as described as being preferred) together is in the range from 0.1 wt.-%, to 6 wt.-%, based on the total weight of the working solution, preferably is in the range from 0.2 wt.-%, to 5 wt.-%, more preferably is in the range from 0.3 wt.-%, to 4 wt.-%, even more preferably in the range from 0.4 wt.-%, to 3.7 wt.-%, most preferably is in the range from 0.5 wt.-%, to 3.5 wt.-%.

Own experiments have shown that the individual presence of the one or more than one triazine silane compound according to the present invention and the one or more than one triazine silane oligomer according to the present invention varies over time. In a freshly prepared working solution typically the total weight of triazine silane compounds of the present invention is higher than the total weight of triazine silane oligomers of the present invention. However, over time upon utilizing the working solution the total weight of said triazine silane oligomers drastically increases, possibly even up to the point that the total weight of said triazine silane oligomers is higher than the total weight of said triazine silane compounds. Furthermore, the handling of the working solution of the present invention also affects the total weights of said compounds and oligomers, respectively. For example, a significant drag out during utilizing the working solution and a corresponding replenishment with fresh working solution typically leads to a steady state condition in terms of triazine silane compound(s) vs. triazine silane oligomer(s).

Most preferably, the working solution of the present invention comprises

- one or more than one triazine silane compound according to the present invention (as described throughout the present text, preferably as described as being preferred), and
- one or more than one triazine silane oligomer according to the present invention (as described throughout the present text, preferably as described as being preferred). Thus, a respective working solution comprising at least one compound and at least one oligomer is most preferred.

The working solution of the present invention has a pH in the range from 2 to 14. Preferred is a working solution of the present invention, wherein the pH is in the range from 3 to 14, more preferably in the range from 4.0 to 13.5.

Preferred is a working solution of the present invention, wherein in said solution water is present in a total amount in the range from 5 wt.-%, to 90 wt.-%, based on the total weight of the working solution, preferably in a total amount in the range from 10 wt.-%, to 85 wt.-%, more preferably in a total amount in the range from 15 wt.-%, to 80 wt.-%.

In order to sufficiently solubilize the triazine silane compounds of the present invention and the triazine silane oligomers of the present invention in the working solution of the present invention, one or more than one water miscible organic solvent is present. Preferred is a working solution of the present invention, wherein in said solution the one or more than one water miscible organic solvent is present in a total amount in the range from 5 wt.-% to 90 wt.-%, based on the total weight of the working solution, preferably in a total amount in the range from 10 wt.-%, to 85 wt.-%, more preferably in a total amount in the range from 15 wt.-%, to 80 wt.-%.

As mentioned above, in the context of the present invention triazine silane compounds of the present invention as well as triazine silane oligomers of the present invention are initially free of halides. This means on the one hand that said compounds and oligomers, respectively, are in itself free of halide atoms because no educts containing halogen atoms are utilized, and on the other hand no halide ions are present in the immediate synthesis environment. However, in a few cases it is preferred that the working solution of the present invention comprises a precisely defined amount of halide ions. Therefore, in some cases a working solution of the present invention is preferred further comprising (d) halide ions, preferably chloride ions.

However, in other cases it is preferred that the working solution of the present invention is substantially free of, preferably does not comprise, chloride ions, more preferably is substantially free of, preferably does not comprise, halide ions.

One or more than one water miscible organic solvent is present in both the storage solution of the present invention and the working solution of the present invention. Preferred is an storage solution according to the present invention (as described throughout the present text, preferably as described as being preferred), or a working solution according to the present invention (as described throughout the present text, preferably as described as being preferred), wherein the one or more than one water miscible organic solvent comprises a water-miscible organic solvent selected from the group consisting of C1 to C4 alcohols, ethers, glycol ethers, and mixtures thereof, preferably selected from the group consisting of

- C1 to C3 alcohols,
- cyclic and non-cyclic ethers such as diethyl ether, tetrahydrofuran, 1,4-dioxane, and mixtures thereof, preferably 1,4-dioxane, tetrahydrofuran and mixtures thereof,
- $HO-(CH_2-CH_2O)_p-T$, wherein
  - p is 1, 2, 3, or 4, preferably 1 or 2, and
  - T denotes C1 to C5 alkyl, preferably C3 to C5 alkyl,
- and mixtures thereof, more preferably
- selected from the group consisting of methanol, diethylene glycol monobutyl ether, ethylene glycol monobutyl ether, and mixtures thereof, even more preferably selected from the group consisting of diethylene glycol monobutyl ether, ethylene glycol monobutyl ether, and mixtures thereof.

The above defined water-miscible organic solvents likewise apply to the synthesis method of the present invention (see text below).

In each case, glycol ethers are more preferred than alcohols. Glycol ethers typically provide an improved stabilization compared to said alcohols. Furthermore, alcohols in general exhibit a low flash point compared to glycol ethers, which makes alcohols potentially dangerous in terms of fire hazard. A comparatively high flash point is usually desired in order to prevent an ignition. Thus, glycol ethers typically provide the desired solubility, stability and security. This principle preferably applies likewise to the mixture of the present invention, the storage solution of the present invention, and the synthesis method of the present invention (see text below).

Preferred is a storage solution according to the present invention (as described throughout the present text, preferably as described as being preferred), or a working solution according to the present invention (as described throughout the present text, preferably as described as being preferred), wherein all triazine silane compounds according to the present invention (as described throughout the present text, preferably as described as being preferred) and all triazine silane oligomers according to the present invention (as described throughout the present text, preferably as described as being preferred) represent at least 70 wt.-%, of the total weight of all triazine silane compounds and oligomers in said storage solution and said working solution, respectively, preferably represent at least 80 wt.-%, more preferably represent at least 90 wt.-%, even more preferably represent at least 93 wt.-%, most preferably represent at least 95 wt.-%, even most preferably represent at least 98 wt.-%. It is most preferred that no other triazine silane compounds or oligomers are present, except those according to the present invention. This also means that the absolute total amounts of triazine silane compounds and triazine silane oligomers together (as defined in the very text above) very preferably apply with the proviso that no other triazine silane compounds and triazine silane oligomers are present in the storage solution of the present invention and working solution of the present invention, respectively.

Furthermore, preferred is a storage solution according to the present invention (as described throughout the present text, preferably as described as being preferred), or a working solution according to the present invention (as described throughout the present text, preferably as described as being preferred), wherein all triazine silane compounds according to the present invention (as described throughout the present text, preferably as described as being preferred) and all triazine silane oligomers according to the present invention (as described throughout the present text, preferably as described as being preferred) represent at least 51 mol-% of all compounds comprising at least one silicon atom in said storage solution and said working solution, respectively, preferably represent at least 60 mol-%, more preferably represent at least 70 mol-%, most preferably represent at least 80 mol-%, even most preferably represent at least 90 mol-%.

The present invention also relates to a synthesis method for a triazine silane compound of formula (II)

A synthesis method for a triazine silane compound of formula (II)

(II)

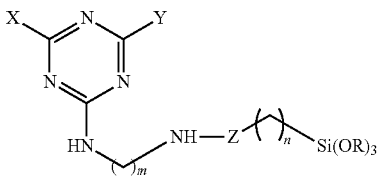

wherein X and Y are independently selected from the group consisting of $NH_2$, $NH(NH_2)$, $NH(CH_2)_oNH_2$, SH, $SCH_3$, and $OCH_3$; Z is selected from the group consisting of

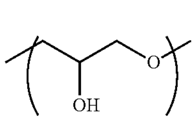 and 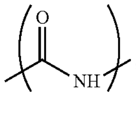, m is an integer in the range from 2 to 12,
n is an integer in the range from 1 to 12,
o is an integer in the range from 2 to 12, R independently denotes $(CH_2CH_2—O)_p—T$, wherein independently p is 0, 1, 2, 3, or 4, and T denotes H or C1 to C5 alkyl.

the synthesis method comprising the steps of (i) providing a compound of formula (III)

(III)

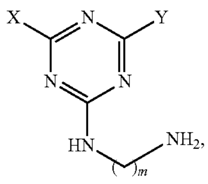

wherein X and Y are independently selected from the group consisting of $NH_2$, $NH(NH_2)$, $NH(CH_2)_oNH_2$, SH, $SCH_3$, and $OCH_3$; and m is an integer in the range from 2 to 12, (ii) providing a silane compound selected from the group of (ii-a) a silane compound of formula (IV)

(IV)

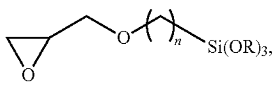

and (ii-b) a silane compound of formula (V)

$$OCN—(CH_2)_n—Si(OR)_3, \quad (V)$$

wherein in formula (IV) or (V)

R denotes $(CH_2—CH_2—O)_p—T$, wherein independently p is 0, 1, 2, 3, or 4, and

T denotes C1 to C5 alkyl, and n is an integer in the range from 1 to 12, o is an integer in the range from 2 to 12, (iii) reacting in a solvent said intermediate of formula (III) with said silane compound such that above defined compound of formula (II) results, and (iv) optionally hydrolyzing the compound of formula (II) obtained in step (iii) such that at least one of R is $(CH_2—CH_2—O)_m—Z$ with m=zero and Z=H.

The above mentioned regarding the triazine silane compound of the present invention (preferably as described as being preferred) preferably applies likewise to the synthesis method of the present invention, e.g. regarding very preferred triazine silane compounds of the present invention.

The synthesis of compounds of formula (III) that are provided in step (i) is known in the literature.

The synthesis of compounds of formula (III)

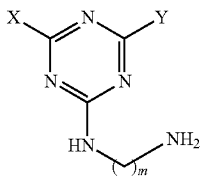

(III)

preferably comprises the steps of (A-i) providing a triazine compound of formula (IX)

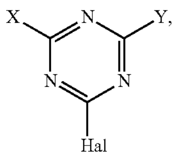

(IX)

wherein X and Y are independently selected from the group consisting of $NH_2$, $NH(NH_2)$, $NH(CH_2)_oNH_2$, SH, $SCH_3$, and $OCH_3$; and o is an integer in the range from 2 to 12, and Hal is selected from Cl, Br, and I; preferably, Hal is Cl, (A-ii) providing a diamine $H_2N(CH_2)_mNH_2$ (A-iii) reacting in a solvent said triazine compound with said diamine such that an intermediate of formula (III) results

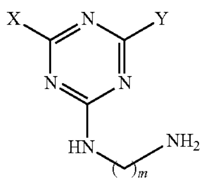

(III)

(A-iv) optionally, isolating/purifying the intermediate of formula (III).

A preferred synthesis is the synthesis of compound of formula (IIIa)

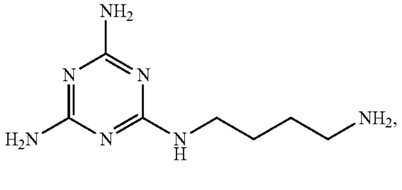

(IIIa)

which comprises the steps of (A-i) providing a triazine compound of formula (IXa)

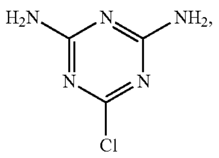

(IXa)

(A-ii) providing the diamine $H_2N(CH_2)_4NH_2$, i.e. 1,4-diaminobutane, (A-iii) reacting in a solvent said triazine compound with said diamine such that the compound of formula (IIIa) results

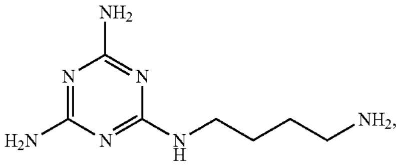

(IIIa)

(A-iv) optionally, isolating/purifying the intermediate of formula (IIIa).

Step (iv) is optional and includes the presence of at least some water in order to hydrolyze the compound obtained in step (iii) of the method of the present invention. Preferably, such water is added after step (iii) in an additional step, e.g. step (iv). If such a compound is desired (m=zero and Z=H), step (iv) is not optional. Very preferred is a synthesis method of the present invention, wherein in step (iii) the solvent comprises an organic solvent, more preferably is one or more than one organic solvent, most preferably is one or more than one water miscible organic solvent. In many cases a synthesis method of the present invention is preferred, wherein in step (iii) the solvent is one or more than one solvent selected from the group consisting of C1 to C4 alcohols, glycol ethers, and mixtures thereof, preferably selected from the group consisting of C1 to C3 alcohols, $HO—(CH_2—CH_2—O)_p—T$, wherein p is 1, 2, 3, or 4, preferably is 1 or 2, and T denotes C1 to C5 alkyl, preferably C3 to C5 alkyl, and mixtures thereof, more preferably selected from the group consisting of methanol, diethylene glycol monobutyl ether, ethylene glycol monobutyl ether, and mixtures thereof, even more preferably selected from the group consisting of diethylene glycol monobutyl ether, ethylene glycol monobutyl ether, and mixtures thereof.

Generally, glycol ethers are more preferred than above defined alcohols (for reasons see text above). Thus, a respective synthesis method of the present invention is preferred.

Preferred is a synthesis method of the present invention (in particular as described before), wherein the solvent in step (iii) is substantially free of, preferably does not comprise, water.

Preferably, the solvent in step (iii) is one or more than one organic solvent and after step (iii) of the method of the present invention a mixture according to the present invention is obtained (for the mixture see text above). The aforementioned regarding the mixture of the present invention applies likewise to the synthesis method of the present invention.

Preferred is a synthesis method of the present invention, wherein the total molar ratio of the compound of formula (III) to the compound of formula (IV) or (V) is in the range from 1:0.7 to 1:1.3, preferably in the range from 1:0.80 to 1:1.2, more preferably in the range from 1:0.9 to 1:1.2, most preferably in the range from 1:0.95 to 1:1.05. If the total molar ratio is significantly higher than 1:1.3 the synthesis product is not sufficiently stable. If the total molar ratio is significantly lower than 1:0.7 too much unreacted educts are present in the synthesis product, which is not desired because the desired species is the triazine silane compound comprising the triazine and the silane moiety. This principle preferably applies likewise to the mixture of the present invention, the storage solution of the present invention, and the working solution of the present invention.

Preferred is a synthesis method of the present invention, wherein in step (iii) the temperature is in the range from 50° C. to 90° C., preferably in the range from 60° C. to 85° C.

Preferred is a synthesis method of the present invention, wherein in step (i) the triazine compound of formula (III) is provided as a suspension. This means that it is preferred to suspend the triazine compound of formula (III) in at least one solvent such that said triazine compound and said at least one solvent form said suspension. For that it is preferred that the at least one solvent is one or more than one organic solvent, preferably is one or more than one water miscible organic solvent. Very preferably the at least one solvent utilized to form said suspension is identical to the solvent utilized in step (iii). Most preferred, the triazine compound of formula (III) is suspended in one or more than one solvent selected from the group consisting of C1 to C4 alcohols, glycol ethers, and mixtures thereof, preferably selected from the group consisting of C1 to C3 alcohols, cyclic and non-cyclic ethers such as diethyl ether, tetrahydrofuran, 1,4-dioxane, and mixtures thereof, preferably 1,4-dioxane, tetrahydrofuran and mixtures thereof, —HO—$(CH_2—CH_2—O)_p$—T, wherein p is 1, 2, 3, or 4, preferably is 1 or 2, and T denotes C1 to C5 alkyl, preferably C3 to C5 alkyl, and mixtures thereof, more preferably selected from the group consisting of methanol, diethylene glycol monobutyl ether, ethylene glycol monobutyl ether, and mixtures thereof, most preferably selected from the group consisting of diethylene glycol monobutyl ether, ethylene glycol monobutyl ether, and mixtures thereof.

Preferred is a synthesis method of the present invention, wherein in step (iii) the reacting is carried out for 1 hour to 48 hours, preferably for 3 hours to 30 hours, more preferably for 5 hours to 24 hours.

The present invention also relates to the specific use of above mentioned working solution of the present invention (as described throughout the present text, preferably as described as being preferred) as a surface treatment solution, preferably for treating a metal surface and/or a surface of an organic material. Preferably both, the metal surface and the organic material are included in the manufacturing of electronic components.

Due to the method according to the invention the adhesion strength (e.g. peel strength) between a metal and an organic material can be increased without using any etch-cleaning steps. But some cases—especially cases where a surface roughness of the metal surface does not affect the quality of the circuits—a further etch-cleaning step can be performed. In this case the adhesion strength between a metal and an organic material can be increased even further.

The contacting in step (ii) can be applied as dip application. Dip application means that the solution is provided in form of a bath into which the copper, copper alloy or copper oxide are dipped.

In the alternative, step (ii) can be applied as spray application. Spray application means that the solution is transferred into a spray dispenser and then sprayed onto the copper, copper alloy or copper oxide.

In the alternative, step (ii) can be applied as coating application such as bar coating, spin coating and curtain coating.

The method according to the invention is preferably performed at temperatures of from 5° C. to 60° C., more preferably from 10° C. to 40° C., even more preferably from 20° C. to 30° C. The method according to the invention is preferred, additionally comprising the following step before conducting step (ii): (i-a) contacting the at least one section of said metal, metal alloy or metal oxide with an etch-cleaning solution, preferably an etch-cleaning solution containing one or more than one acid and/or one or more than one oxidizing agent, more preferably an etch-cleaning solution containing a mixture of an inorganic acid and a peroxide (preferably a mixture of sulfuric acid and hydrogen peroxide).

According to the present invention it is preferred, when the oxidizing agent is a peroxide, more preferably when the peroxide is hydrogen peroxide.

According to the present invention it is preferred, when the etch-cleaning solution comprises in addition to the acid and/or to the one or more than one oxidizing agent a corrosion inhibitor.

The method according to the invention is preferred, additionally comprising the following step before conducting step (ii): (i-b) contacting the at least one section of said metal, metal alloy or metal oxide with a (preferably second) etch-cleaning solution. In case step (i-b) is carried out after step (i-a) the used etch-cleaning solution is the second etch-cleaning solution. In case step i-b is carried out without a previous etch-cleaning step, the used etch-cleaning solution is the first etch-cleaning solution.

According to the present invention the second etch-cleaning solution comprises an iron (III) salt or an iron (III) complex, more preferably the second etch-cleaning solution comprises ferric sulfate ($Fe_2(SO_4)_3$), ferric chloride ($FeCl_3$), bromide, ferric ($FeBr_3$), ferric nitrate ($Fe(NO_3)_3$), ferric acetate ($Fe(OC(O)CH_3)_3$), ($Fe(OH)_3$), or mixtures thereof, even more preferably the second etch-cleaning solution comprises ferric sulfate ($Fe_2(SO_4)_3$). The Ferric ion is preferably contained at a concentration in the range of 1 to 100 g/l, preferably from 1 to 50 g/l, and more preferably from 1 to 30 g/l.

In an alternative, according to the present invention the second etch-cleaning solution comprises an inorganic acid, more preferably the second etch-cleaning solution comprises sulfuric acid, hydrochloric acid or mixtures thereof, even more preferably the second etch-cleaning solution comprises sulfuric acid.

According to the present invention the second etch-cleaning solution preferably comprises in addition to the iron (III) salt or an iron (III) complex an acid, preferably sulfuric acid.

According to the present invention, a typical metal, metal alloy or metal oxide removal during step i-a is less than 2 μm, preferably, the removal is of from 0.1 μm to 1.5 μm, more preferably, the removal is of from 0.2 μm to 1.2 μm, even more preferably, the removal is of from 0.4 μm to 1.1

μm, most preferably, the removal is of from 0.5 μm to 1.0 μm; and resulting average surface roughness Ra is a maximum of 100 nm.

According to the present invention, a typical metal, metal alloy or metal oxide removal during step i-b is less than 20 nm and resulting average surface roughness Ra is a maximum of 10 nm, preferably, a maximum of 5 nm.

The method according to the invention is preferred, additionally comprising the following step before conducting step (ii): (i-c) contacting the at least one section of said metal, metal alloy or metal oxide with a solution, preferably a sodium hydroxide solution. It is preferred if the solution contain metal complexing agents.

In some embodiments of the present invention it is preferred if the solution used in step i-c additionally contains sodium chlorite. The use of sodium chlorite in the solution used in step i-c is especially preferred if in step i-b no iron (III) salt or an iron (III) complex is used or if step i-b is not performed during the method according to the present invention.

The order of the steps (i-a), (i-b), and (i-c) may vary. The method according to the invention can be carried out in the following order: (i-a), (i-b), (i-c), or (i-a), (i-c), (i-b), or (i-b), (i-a), (i-c), or (i-b), (i-c), (i-a), or (i-c), (i-a), (i-b), or (i-c), (i-b), (i-a). The order (i-a), (i-b), (i-c) is preferred. It is also possible that none, one or two of the steps (i-a), (i-b), (i-c) are performed in the method according to the invention.

The method according to the invention is preferred, wherein the organic material applied in step (iii) is an organic polymer.

The method according to the invention is preferred, wherein the organic material is applied in step (iii) by laminating the organic material onto at least the contacted section of the metal, metal alloy or metal oxide.

The method according to the invention is preferred, comprising after step (iii) the additional step: (iv) subjecting the substrate and the organic material to a heat treatment with a temperature in the range from 142° C. to 420° C., preferably in the range from 145° C. to 300° C., more preferably in the range from 150° C. to 220° C.

The method according to the invention is preferred, wherein after step (ii), after step (i-a), after step (i-b) and/or after step (i-c), a rinsing of the at least one section of the metal, metal alloy or metal oxide is performed, wherein the metal, metal alloy or metal oxide is preferably rinsed with water. It is preferred if the water that is used during rinsing after step (ii) has a pH-value in the range from 4 to 10, preferably in the range from 5 to 9, more preferably in the range from 6 to 8, most preferably in the range from 6.5 to 7.5.

The method according to the invention is preferred, wherein after step (ii), after step (i-a), after step (i-b) and/or after step (i-c), a drying of the at least one section of the metal, metal alloy or metal oxide is performed.

The method according to the invention is preferred, wherein the metal, metal alloy or metal oxide is copper, aluminum, titanium, nickel, tin, iron, silver, gold, an alloy comprising at least one of the aforementioned metals (or an alloy comprising just the aforementioned metals), or a metal oxide of at least one of the aforementioned metals. The method according to the invention is especially preferred wherein the metal is copper, the metal alloy contains copper and the metal oxide is or contains a copper oxide.

A method according to the present invention is especially preferred comprising the following steps in this order:

(i) providing a substrate, comprising the metal, metal alloy or metal oxide on at least one side of the substrate, (i-a) optionally contacting at least one section of said metal, metal alloy or metal oxide with an etch-cleaning solution, preferably an etch-cleaning solution containing one or more than one acid and/or one or more than one oxidizing agent, more preferably an etch-cleaning solution containing a mixture of an inorganic acid and a peroxide, and optionally followed by rinsing of the at least one section of the metal, metal alloy or metal oxide, (i-b) optionally contacting the at least one section of said metal, metal alloy or metal oxide with a second etch-cleaning solution, wherein the second etch-cleaning solution preferably comprises ferric sulfate and/or sulfuric acid, and optionally followed by rinsing of the at least one section of the metal, metal alloy or metal oxide (preferably with water), (i-c) optionally contacting the at least one section of said metal, metal alloy or metal oxide with an alkaline solution, and optionally followed by rinsing of the at least one section of the metal, metal alloy or metal oxide (preferably with water), i) contacting of the at least one section of said metal, metal alloy or metal oxide with A) triazine silane compound of formula (I)

(I)

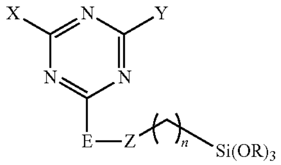

wherein

X and Y are independently selected from the group consisting of $NH_2$, $NH(NH_2)$, $NH(CH_2)_oNH_2$, SH, $SCH_3$, and $OCH_3$;

E is selected from the group consisting of —S— and —NH—$(CH_2)_m$—NH—;

Z is selected from the group consisting of

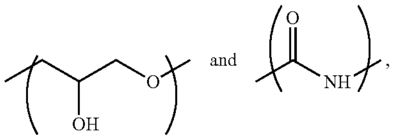

m is an integer in the range from 2 to 12, n is an integer in the range from 1 to 12, o is an integer in the range from 2 to 12, R independently denotes $(CH_2—CH_2—O)_p$—T, wherein independently p is 0, 1, 2, 3, or 4, and T denotes H or C1 to C5 alkyl, and/or B) a triazine silane oligomer obtained by reacting the triazine silane compounds of formula (I) with each other in the presence of water such that the triazine silane oligomer comprises at least one silicon-oxygen-silicon moiety, wherein in the compounds of formula (I) used for the reaction to form the triazine silane oligomer X denotes H, $CH_3$, $NH_2$, $NH(NH_2)$, $NH(CH_2)_oNH_2$, NH(NHU), SH, $SCH_3$, $OCH_3$, NHU, or SU, wherein o is an integer in the range from 2 to 12, and Y and U have the meanings given above, and optionally followed by rinsing of the at least one section of the metal, metal alloy or metal oxide (preferably with water), (iii) applying the organic material such that the at least one section of the metal, metal alloy or metal oxide contacted with the triazine silane compound and/or the triazine silane oligomer during step (ii) is in contact with the applied organic material, and (iv) optionally subjecting the substrate and the organic material to a heat treatment with a temperature in the range from 142° C. to 420° C., preferably in the range from 145° C. to 300° C., more preferably in the range from 150° C. to 220° C., wherein preferably the metal is copper, the metal alloy contains copper and the metal oxide is or contains a copper oxide.

A method according to the present invention is preferred, wherein the substrate is a non-conductive substrate and/or the organic material is a non-conductive organic material, preferably a non-conductive organic polymer.

EMBODIMENTS

The invention is described by the following embodiments.

A. A triazine silane compound of formula (I)

wherein (I)

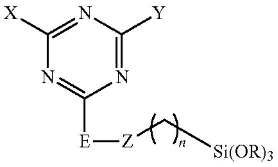

X and Y are independently selected from the group consisting of $NH_2$, $NH(NH_2)$, $NH(CH_2)_oNH_2$, SH, $SCH_3$, and $OCH_3$;

E is selected from the group consisting of —S— and —NH—$(CH_2)_m$—NH—;

Z is selected from the group consisting of

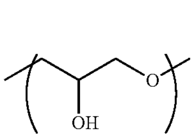 and 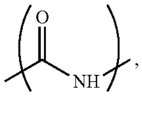, m is an integer in the range from 2 to 12, n is an integer in the range from 1 to 12, o is an integer in the range from 2 to 12, R independently denotes $(CH_2CH_2—O)_p$—T, wherein independently p is 0, 1, 2, 3, or 4, and T denotes H or C1 to C5 alkyl.

B. A triazine silane compound of embodiment A, wherein E is —NH—$(CH_2)_m$—NH—, exhibiting a structure of formula (II)

wherein (II)

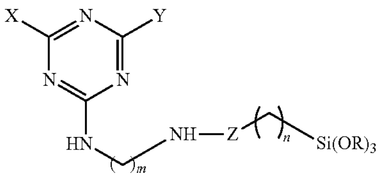

X and Y are independently selected from the group consisting of $NH_2$, $NH(NH_2)$, $NH(CH_2)_oNH_2$, SH, $SCH_3$, and $OCH_3$;

Z is selected from the group consisting of

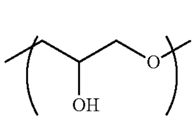 and 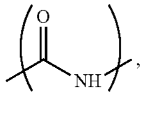, m is an integer in the range from 2 to 12, n is an integer in the range from 1 to 12, o is an integer in the range from 2 to 12, R independently denotes $(CH_2—CH_2—O)_p$—T, wherein independently p is 0, 1, 2, 3, or 4, and T denotes H or C1 to C5 alkyl.

C. The compound of any ones of embodiments A to B, wherein X and Y are independently selected from the group consisting of $NH_2$, $NH(NH_2)$, $NH(CH_2)_oNH_2$, SH, and $SCH_3$, wherein o is an integer in the range from 2 to 12, preferably X and Y are $NH_2$.

D. A triazine silane oligomer obtained by reacting in the presence of water triazine silane compounds of any ones of embodiments A to C.

E. A mixture comprising (a) one or more than one triazine silane compound according to any one of embodiments A to C, and/or one or more than one triazine silane oligomer according to embodiment D, (b) one or more than one organic solvent.

F. A storage solution comprising (a) one or more than one triazine silane compound according to any one of embodiments A to C, and optionally one or more than one triazine silane oligomer according to embodiment D, (b) optionally water, (c) one or more than one water miscible organic solvent, with the proviso that, if water is present, the pH is 9 or higher.

G. The storage solution according to embodiment F, wherein in the solution the total amount of all triazine silane compounds according to any one of embodiments A to C and all triazine silane oligomers according to embodiment 4 together is in the range from 0.2 wt.-%, to 40 wt.-%, based on the total weight of the storage solution, preferably is in the range from 0.5 wt.-%, to 35 wt.-%, more preferably is in the range from 0.7 wt.-%, to 30 wt.-%, even more preferably is in the range from 0.8 wt.-%, to 30 wt.-%, most preferably is in the range from 0.9 wt.-%, to 25 wt.-%.

H. A working solution having a pH in the range from 2 to 14, the solution comprising (a) one or more than one triazine silane compound according to any one of embodiments A to C, and/or optionally, one or more than one triazine silane oligomer according to embodiment D, (b) optionally, water, (c) one or more than one water miscible organic solvent, wherein in said working solution the total amount of all triazine silane compounds according to any one of embodiments A to C and all triazine silane oligomers according to embodiment D together is 5 wt.-%, or less, based on the total weight of the working solution.

I. The storage solution according to embodiment F or G, or the working solution according to embodiment H, wherein the one or more than one water miscible organic solvent comprises a water-miscible organic solvent selected from the group consisting of C1 to C4 alcohols, ethers, glycol ethers, and mixtures thereof, preferably selected from the group consisting of C1 to C3 alcohols, diethyl ether, 1,4-dioxane, tetrahydrofuran and mixtures thereof, $HO—(CH_2—CH_2—O)_p—T$, wherein p is 1, 2, 3, or 4, preferably 1 or 2, and T denotes C1 to C5 alkyl, preferably C3 to C5 alkyl, and mixtures thereof, more preferably selected from the group consisting of methanol, diethylene glycol monobutyl ether, ethylene glycol monobutyl ether, and mixtures thereof, even more preferably selected from the group consisting of diethylene glycol monobutyl ether, ethylene glycol monobutyl ether, and mixtures thereof.

J. A synthesis method for a triazine silane compound of formula (II)

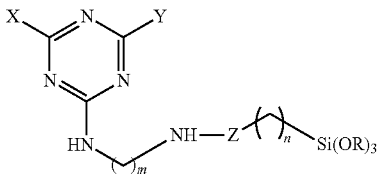

(II)

wherein X and Y are independently selected from the group consisting of $NH_2$, $NH(NH_2)$, $NH(CH_2)_oNH_2$, SH, $SCH_3$, and $OCH_3$ wherein o is an integer in the range from 2 to 12;

Z is selected from the group consisting of

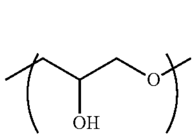 and 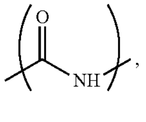, m is an integer in the range from 2 to 12, n is an integer in the range from 1 to 12, R independently denotes $(CH_2—CH_2—O)_p—T$, wherein independently p is 0, 1, 2, 3, or 4, and T denotes H or C1 to C5 alkyl.

the synthesis method comprising the steps of (i) providing a compound of formula (III)

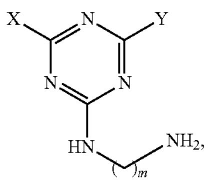

(III)

(ii) providing a silane compound selected from the group of (ii-a) a silane compound of formula (IV) and

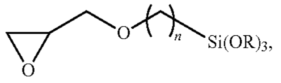

(IV)

(ii-b) a silane compound of formula (V)

$$OCN—(CH_2)_n—Si(OR)_3, \quad (V)$$

wherein in formula (IV) or (V)

R denotes $(CH_2—CH_2—O)_p—T$, wherein independently p is 0, 1, 2, 3, or 4, and

T denotes C1 to C5 alkyl, and n is an integer in the range from 1 to 12, (iii) reacting in a solvent said intermediate of formula (III) with said silane compound such that above defined compound of formula (II) results, and (iv) optionally hydrolyzing the compound of formula (II) obtained in step (iii) such that at least one of R is $(CH_2—CH_2—O)_m—Z$ with m=zero and Z=H.

K. Use of the working solution according to embodiment H as a surface treatment solution.

L. A method for increasing adhesion strength between a surface of a metal, a metal alloy or a metal oxide and a surface of an organic material comprising the following steps in this order:

(i) providing a substrate, comprising the metal, metal alloy or metal oxide on at least one side of the substrate, (ii) contacting at least one section of said metal, metal alloy or metal oxide with A) a triazine silane compound of formula (II) formula (I)

wherein

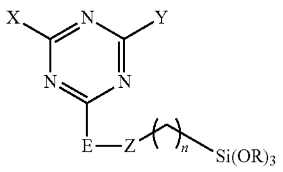

(I)

X and Y are independently selected from the group consisting of $NH_2$, $NH(NH_2)$, $NH(CH_2)_oNH_2$, SH, $SCH_3$, and $OCH_3$;

E is selected from the group consisting of —S— and —NH—$(CH_2)_m$—NH—;

Z is selected from the group consisting of

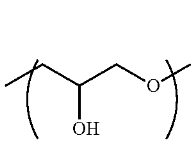 and 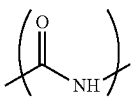, m is an integer in the range from 2 to 12, n is an integer in the range from 1 to 12, o is an integer in the range from 2 to 12, R independently denotes $(CH_2—CH_2—O)_p$—Z, wherein independently p is 0, 1, 2, 3, or 4, and T denotes H or C1 to C5 alkyl and/or B) a triazine silane oligomer obtained by reacting the triazine silane compounds of formula (II) with each other in the presence of water such that the triazine silane oligomer comprises at least one silicon-oxygen-silicon moiety, and (iii) applying the organic material such that the at least one section of the metal, metal alloy or metal oxide contacted with the triazine silane compound and/or the triazine silane oligomer during step (ii) is in contact with the applied organic material.

M. The method according to embodiment L, wherein the solution further comprises one or more than one water miscible organic solvent.

N. The method according to embodiment M, wherein the one or more than one water miscible organic solvent comprises a water-miscible organic solvent selected from the group consisting of C1 to C4 alcohols, ethers, glycol ethers, and mixtures thereof, preferably selected from the group consisting of C1 to C3 alcohols, HO—$(CH_2—CH_2—O)_p$—T, wherein p is 1, 2, 3, or 4, preferably 1 or 2, and T denotes C1 to C5 alkyl, preferably C3 to C5 alkyl, and mixtures thereof, more preferably selected from the group consisting of methanol, diethylene glycol monobutyl ether, ethylene glycol monobutyl ether, and mixtures thereof, even more preferably selected from the group consisting of diethylene glycol monobutyl ether, ethylene glycol monobutyl ether, and mixtures thereof.

O. The method according to embodiment M or N, wherein a solution of the triazine silane compound of formula (II) and/or the triazine silane oligomer is used in step (ii), and wherein the solution preferably comprises 5 to 90 wt.-%, water, based on the total weight of the solution.

P. The method according to any one of the embodiments M to O, wherein the total amount of the triazine silane compounds and the triazine silane oligomers together is 5 wt.-%, or less, based on the total weight of the solution.

Q. The method according to any one of the embodiments M to P, wherein the solution has a pH in the range from 2 to 14, preferably in the range from 3 to 14, more preferably in the range from 4.0 to 13.5.

R. The method according to any of the embodiments L to Q additionally comprising the following step before conducting step (ii):

(i-a) contacting the at least one section of said metal, metal alloy or metal oxide with an etch-cleaning solution, preferably an etch-cleaning solution containing one or more than one acid and/or one or more than one oxidizing agent, more preferably an etch-cleaning solution containing a mixture of an inorganic acid and a peroxide.

S. The method according to any of the embodiments L to R additionally comprising the following step before conducting step (ii):

(i-b) contacting the at least one section of said metal, metal alloy or metal oxide with a (preferably second) etch-cleaning solution, preferably comprising an iron (III) salt or an iron (III) complex.

T. The method according to any of the embodiments L to S additionally comprising the following step before conducting step (ii):

(i-c) contacting the at least one section of said metal, metal alloy or metal oxide with a solution.

U. The method according to any of the embodiments L to T, wherein the organic material applied in step (iii) is an organic polymer.

V. The method according to any of the embodiments L to U, wherein the organic material is applied in step (iii) by laminating the organic material onto at least the contacted section of the metal, metal alloy or metal oxide.

W. The method according to any of the embodiments L to V, comprising after step (iii) the additional step:

(iv) subjecting the substrate and the organic material to a heat treatment with a temperature in the range from 142° C. to 420° C., preferably in the range from 145° C. to 300° C., more preferably in the range from 150° C. to 220° C.

X. The method according to any of the embodiments L to W, wherein after step (ii), after step (i-a), after step (i-b) and/or after step (i-c), a rinsing of the at least one section of the metal, metal alloy or metal oxide is performed, wherein the metal, metal alloy or metal oxide is preferably rinsed with water.

Y. The method according to any of the embodiments L to X, wherein after step (ii), after step (i-a), after step (i-b) and/or after step (i-c), a drying of the at least one section of metal, metal alloy or metal oxide is performed.

Z. The method according to any of the embodiments L to Y, wherein the metal, metal alloy or metal oxide is copper, aluminum, titanium, nickel, tin, iron, silver, gold, an alloy comprising at least one of the aforementioned metals, or a metal oxide of at least one of the aforementioned metals.

AA. The method according to any of the embodiments L to Z, wherein the contacting time in step (ii) is from 5 seconds to 30 minutes, preferably from 7 seconds to 20 minutes, more preferably from 10 seconds to 10 minutes, even more preferably from 12 seconds to 5 minutes, most preferably from 15 seconds to 120 seconds.

The invention is further explained by the following non-limiting examples.

EXAMPLES

A) Synthesis of triazine silane compounds of formula (VI):

(VI)

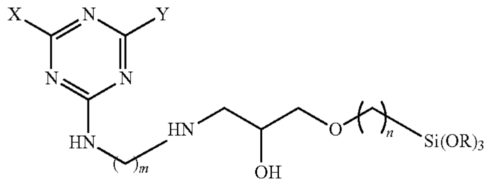

1) Synthesis of triazine silane compound of formula (VIa):

(VIa)

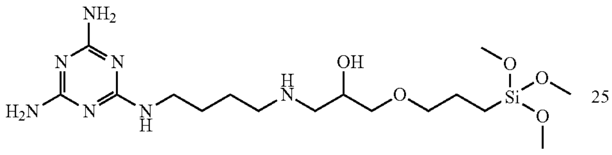

10.0 g (50.7 mmol) N2-(4-aminobutyl)-1,3,5-triazine-2,4,6-triamine were suspended in 92.8 ml diethylene glycol monobutyl ether (DEGBE). This suspension was heated to 80° C. At that temperature 11.98 g (50.7 mmol) 3-glycidoxypropyltrimethoxysilane were added. The reaction mixture was kept at 80° C. for 15 hrs.

Afterwards, a reaction product with a concentration of approximately 20 wt.-%, in DEGBE was obtained. The thus obtained product was utilized without further purification. ESI-MS confirms the formation of a compound comprising three methoxy groups connected to the silicon atom. In addition, compounds comprising one, two, or three DEGBE moieties instead of respective methoxy groups also have been identified.

2) Synthesis of triazine silane compound of formula (VIb):

(VIb)

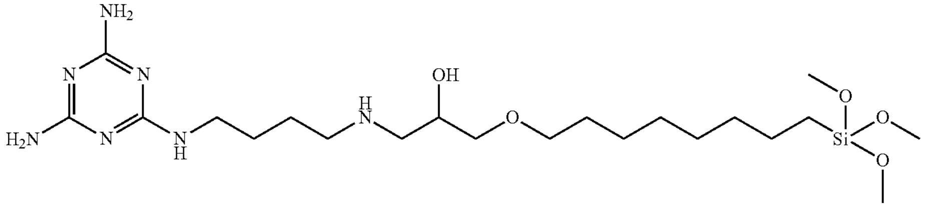

21.0 g (106 mmol) N2-(4-aminobutyl)-1,3,5-triazine-2,4,6-triamine were suspended in 225 ml diethylene glycol monobutyl ether (DEGBE). This suspension was heated to 80° C. At that temperature 32.6 g (106 mmol) [8-(Glycidyloxy)-N-octyl]trimethoxysilan were added. The reaction mixture was kept at 80° C. for 15 hrs.

Afterwards, a reaction product with a concentration of approximately 20 wt.-%, in DEGBE was obtained. The thus obtained product was utilized without further purification.

21.0 g (106 mmol) N2-(4-aminobutyl)-1,3,5-triazine-2,4,6-triamine were suspended in 225 ml diethylene glycol monobutyl ether (DEGBE). This suspension was heated to 80° C. At that temperature 32.6 g (106 mmol) [8-(Glycidyloxy)-N-octyl]trimethoxysilan were added. The reaction mixture was kept at 80° C. for 15 hrs.

Afterwards, a reaction product with a concentration of approximately 20 wt.-%, in DEGBE was obtained. The thus obtained product was utilized without further purification.

ESI-MS confirms the formation of a compound comprising three methoxy groups connected to the silicon atom. In addition, compounds comprising one, two, or three DEGBE moieties instead of respective methoxy groups also have been identified.

B) Synthesis of triazine silane compounds of formula (VII):

(VII)

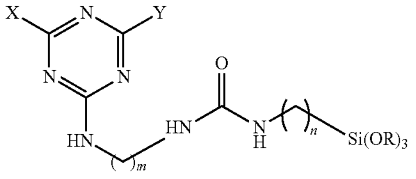

2) Synthesis of triazine silane compound of formula (VIIa):

(VIIa)

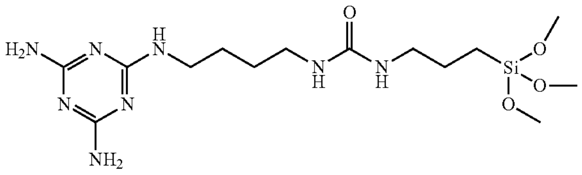

3.0 g (15.2 mmol) N2-(4-aminobutyl)-1,3,5-triazine-2,4,6-triamine were dissolved in 90 ml dioxane. Then 3.29 g (15.2 mmol) (3-isocyanatopropyl)trimethoxysilane were added and the reaction mixture was heated to 50° C. and kept for 20 hrs at that temperature.

Then 55.08 g DEGBE were added and the dioxane was removed by distillation to give the product as a 10 w % solution in DEGBE. The thus obtained product was utilized without further purification.

ESI-MS confirms the formation of a compound comprising three methoxy groups connected to the silicon atom. In addition, compounds comprising one, two, or three DEGBE moieties instead of respective methoxy groups also have been identified.

ESI-MS confirms the formation of a compound comprising three methoxy groups connected to the silicon atom. In addition, compounds comprising one, two, or three DEGBE moieties instead of respective methoxy groups also have been identified.

C) Sample preparation

Samples 1 to 12 (each comprising several identical specimens) were prepared as follows. A comparison example C1 has been prepared according to the same method but without step (ii), i.e. no silane has been applied.

Table 1 gives an overview on the reaction steps which are then described in more detail thereafter. Table 2 provides an additional summary.

TABLE 1

| step | process | make up | Temp | dwell time | remarks |
|---|---|---|---|---|---|
| (i) | Providing copper substrate | | | | |
| | Annealing | | 160° C. | | 1 h |
| (i-a) | Differential Etch (optional) | 25 ml/l Hyperflash 25<br>50 ml/l $H_2SO_4$ 50%<br>65 ml/l $H_2O_2$ 35% | 30° C. | Depending on etch rate | Target etch depth is 0.5 μm & 1 μm |
| | Triple cascade Rinse | water | | | |
| | Dry (optional) | | | Up to dry | |
| (i-b) | $H_2SO_4$ 5 vol % | 130 ml/l $H_2SO_4$ 50% | ambient | 30 s | |
| | Triple cascade Rinse | water | ambient | 20 s | |
| (i-c) | aqueous alkaline solution | | 50° C. | 30-600 s | |
| | Rinse | Water | ambient | 20 s | |
| | Dry (optional) | | | Up to dry | Hot air dryer, e.g. air gun, hair dryer |
| (ii) | Adhesion Promoter | Diff. Silanes | ambient | 60 s | See table with APs |
| | Triple cascade rinse | water | Ambient | 30 s each | |
| | Dry | | | Up to dry | Hot air dryer, e.g. air gun, hair dryer |
| (ii-a) | Baking | | 130 | 30 min | Air ventilated oven |
| (iii) | Lamination | See Table 2 | | | |

Step (i): Providing the Substrate Having on at Least One Surface A Copper Surface Copper foils having a copper surface (150 mm×75 mm×35 μm, plated in house) were used. Under simplified laboratory conditions, copper foils without substrates are used for the examples.

For wedge void and halo investigations plated copper panels were used.

The preparation conditions are as follows:

Electrolytically plated copper type:

foil (adhesion test)

panels (wedge void)

Electrolyte:

Cupracid AC

Plating Parameters:

103 min 1.5 A/dm$^2$=35μm Cu thickness

Step (i-a): Cleaning the Copper Surface with an Etch-Cleaning Solution

The copper surfaces of the copper foils were treated by 25 ml/l Hyperflash 25, 50 ml/l $H_2SO_4$ 50% and 65 ml/l $H_2O_2$ 35% at 30° C. to achieve 0.5 or 1 μm etch depth. After the etch-cleaning the etch-cleaned copper surfaces were rinsed with water for approximately 30 seconds and optionally dried. As a result, etch-cleaned and rinsed copper surfaces were obtained.

Step (i-b): Treating The Copper Surface with Acidic Solution

The copper surfaces of all copper foils for samples 1 to 12 were cleaned at room temperature for 20-30 seconds by using a 5 vol % sulfuric acid.

Step (i-c): Treating The Copper Surface with an Aqueous Alkaline Solution

The copper surfaces of all substrates for samples 1 to 12 were treated with aqueous alkaline solution (50° C., 300 sec). After the treatment the treated copper surfaces of all copper foils were rinsed with cold water for approximately 30 seconds.

Step (ii): Contacting the Copper Surfaces with Silane Compound

Copper surfaces of all substrates for samples 1 to 12 were immersed for 60 sec at 25° C. into a coating solution containing a triazine silane compound and solvents. If water is present, the pH of the coating solution was 7 (adjusted with sulfuric acid). Details are given in Table 2.

Afterwards the resulting copper surfaces of all copper foils were rinsed with water for approximately 30 seconds and dried. As a result, silanized and dried copper surfaces of all copper foils for samples 1 to 12 were obtained.

Step (ii-a): Annealing

The copper foils for samples 1 to 12 containing the silanized copper surfaces were then annealed for 30 minutes at 130° C. to remove remaining moisture from the surface. These substrates containing copper surfaces were subsequently subjected to laminating a build-up film (see text below).

Step (iii): Applying the Organic Material Onto the Copper Surface of the Substrates In a laminating step, an insulating film (see Table 2) was vacuum laminated onto the copper foils of all samples in a clean room with a room temperature in the range from 20 to 25° C. and with a relative humidity of 50 to 60% by using a vacuum laminator.

The conditions for vacuum lamination were as follows: 100° C., vacuum: 30 sec. at 3 hPa, pressure: 30 sec at 0.5 MPa.

After lamination, laminated copper surfaces were obtained.

TABLE 2

| Sample | Silane | Silane concentration | solvent | Insulating film (Lamination) |
|---|---|---|---|---|
| C1 (comparative) | none | n/a | | |
| 1 | (VIa) | 1.5 wt % | MeOH | GX-T31 |
| 2 | (VIa) | 1.5 wt % | DEGBE | GX-T31; GL102 |
| 3 | (VIa) | 1.5 wt % | DEGBE | GX-T31 |
| 4 | (VIa) | 1.5 wt % | DEGBE + $H_2O$ (20:80) | GX-T31 |
| 5 | (VIa) | 1.5 wt % | DEGBE + $H_2O$ (20:80) | GX-T31 |
| 6 | (VIb) | 1.5 wt % | DEGBE | GX-T31; GL102 |
| 7 | (VIa) | 1.5 wt % | DEGBE + $H_2O$ (20:80) | GL102 |
| 8 | (VIa) | 1.5 wt % | DEGBE | GL102 |
| | (VIb) | a) 0.5 wt % b) 1.0 wt % c) 1.5 wt % | DEGBE | GL102 |
| 10 | (VIb) | 1.5 wt % | DEGBE | GL102 |

TABLE 2-continued

| Sample | Silane | Silane concentration | solvent | Insulating film (Lamination) |
|---|---|---|---|---|
| 11 | (VIa) | 1.5 wt % | DEGBE + $H_2O$ (50:50) | GL102 |
| 12 | (VIb) | 1.5 wt % | DEGBE | GL102 |

DEGBE: diethylene glycol monobutyl ether (VIa):

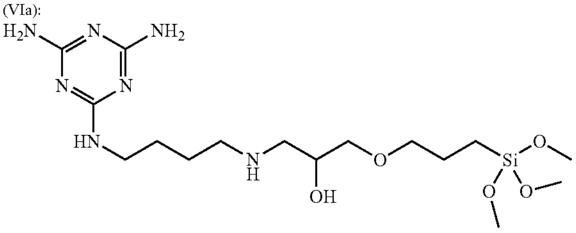

(VIa)

(VIb):

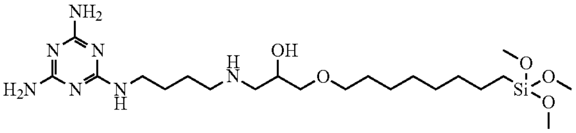

(VIb)

Adhesion evaluation via peel strength test:

For each sample (1 to 12) obtained after the lamination, peel strength was determined:

(1) Initial, (2) after 96 hours HAST (HAST conditions: 130° C., 85% rh, HAST chamber: EHS-221M).

(3) after 12 cycles IR Reflow (thermal reliability, simulation of soldering process with temperature peak at 260° C. In order to determine the peel strength, several strip-type fragments have been prepared from each specimen by adhering the respective copper foils to a rigid board (identical size as the copper foils) in such a way that the rigid board faced the insulating film. As a result, copper surfaces with structurally enforced insulating films were obtained. The obtained copper surfaces with structurally enforced insulating films were then cured in an oven: copper surfaces with GL102 material at 200° C. for 90 minutes and copper surfaces with GX-T31 material at 190° C. for 90 min.

Afterwards, each copper surfaces with structurally enforced insulating films was sliced into said strip-type fragments (10×100 mm, Bugard drilling/routing).

The strip-type fragments were subjected to a peel force measuring machine (Roell Zwick Z010) to individually evaluate the peel strength (angle: 90°, speed: 50 mm/min) which is needed to delaminate the copper surface from its respective structurally enforced insulating films. Typically, the higher the peel strength needed to avoid delamination the better is the adhesion.

The peel strength of samples 1 to 12 are shown in Table 3 below.

TABLE 3

| | | | peel strength in N/cm: | | | | | | | | | | | |
|---|---|---|---|---|---|---|---|---|---|---|---|---|---|---|
| | | | Peel Strength GX-T31 (N/cm) | | | | | | Peel Strength GL102 (N/cm) | | | | | |
| | | | Without step (i-c) | | | With step (i-c) [300 s] | | | Without step (i-c) | | | With step (i-c) [300 s] | | |
| Sample | Silane | solvent | Initial | HAST | Reflow | Initial | HAST | Reflow | Initial | HAST | Reflow | Initial | HAST | Reflow |
| C1 (comparative) | none | | 6.6 | 2.1 | 2.1 | 9.5 | 5 | 4.3 | 6.4 | 1.6 | 4.7 | 7.6 | 3.3 | 5.4 |
| 1 | (VIa) | MeOH | | | | 9.6 | 7 | 5.8 | | | | 7.6 | 4.6 | 6.6 |
| 2 | (VIa) | DEGBE | | | | 8.2 | 7.8 | 7.4 | | | | 6 | 4.2 | 6.2 |

TABLE 3-continued

| | | | peel strength in N/cm: | | | | | | | | | | | |
|---|---|---|---|---|---|---|---|---|---|---|---|---|---|---|
| | | | Peel Strength GX-T31 (N/cm) | | | | | | Peel Strength GL102 (N/cm) | | | | | |
| | | | Without step (i-c) | | | With step (i-c) [300 s] | | | Without step (i-c) | | | With step (i-c) [300 s] | | |
| Sample | Silane | solvent | Initial | HAST | Re-flow | Initial | HAST | Re-flow | Initial | HAST | Re-flow | Initial | HAST | Re-flow |
| 3 | (VIa) | DEGBE | | | | 9.1 | 8.0 | 7.0 | | | | | | |
| 4 | (VIa) | DEGBE + $H_2O$ (20:80) | | | | 8.6 | 6 | 6 | | | | | | |
| 5 | (VIa) | DEGBE + $H_2O$ (20:80) | | | | 9 | 6.2 | 5.8 | | | | | | |
| 6 | (VIb) | DEGBE | | | | 9 | 7.8 | 6 | 6.2 | 4 | 5.5 | 6.8 | 4.5 | 6.0 |
| 7 | (VIa) | DEGBE + $H_2O$ (20:80) | | | | | | | 7 | 1.9 | 6 | 6.8 | 4.8 | 6.3 |
| 8 | (VIa) | DEGBE | | | | | | | 5.8 | 4.0 | 5 | 5.9 | 3.8 | 5.0 |
| 9 | (VIb) | DEGBE | | | | | | | 6.3 | 3.5 | 5.6 | 6.2 | 4.2 | 5.4 |
| 10 | (VIb) | DEGBE | | | | | | | 6.2 | 3.3 | 5.4 | 5.8 | 4.0 | 5.4 |
| 11 | (VIa) | DEGBE + $H_2O$ (50:50) | | | | | | | | | | | | |
| 12 | (VIb) | DEGBE | | | | | | | | | | | | |

DEGBE: diethylene glycol monobutyl ether

The experiments show that the inventive examples exhibit a good adhesion strength, here expressed as peel strength.

Halo and Wedge Void Evaluation

Sample preparation:

In order to evaluate the halo, the copper samples have been prepared by adhering the respective insulating films to copper panels. As a result, copper surfaces with structurally enforced insulating films were obtained.

The obtained copper surfaces with structurally enforced insulating films were then semicured in two steps in the ovens: copper surfaces with GL102 material at 130° C. for 30 minutes followed by 175° C. for 30 minutes; and copper surfaces with GX-T31 material at 100° C. for 30 minutes followed by 170° C. for 30 minutes.

After completing the lamination and semi-curing step, the copper panels were lasered with UV-laser to drill the blind micro vias (BMV). Thereafter, the substrates were subjected to the desmear and reduction condition steps. In particular, these included a sweller treatment under alkaline conditions with Securiganth MV Sweller (Atotech); a permanganate treatment under alkaline conditions with Securiganth MV Etch P (Atotech) and a reduction conditioner treatment under acidic conditions with Securiganth MV Reduction Conditioner (Atotech). After each step the sample were rinsed with water.

The lamination material exhibits a thickness of ca. 10 μm for wedge void and halo and 35 μm in case of adhesion investigations, respectively.

Measurements:

1) Halo Evaluation

The substrates were measured by light microscope (200× magnification; see Table 4). Pictures depicting the halo measurement can be found in FIG. 1.

The investigated test Blind Micro Via's (BMV) are manufactured as a test grid on surface treated and Ajinomoto Buildup Film (ABF) laminated test vehicles by utilizing Laser Drilling technology. The halo data is obtainable after sending the prepared test vehicles through entire Desmear process (Sweller, Permanganate, Reduction Conditioner) as described above.

Halo measurement is performed by camera (CCD) supported light microscopy. Hereby, the microscope must be operated in epi-illumination mode. All image generation must be carried out by using Darkfield (DF) filter setting. A magnification factor of approx. 200× is typically used.

The fully processed test vehicles are firmly installed on the measurement table and the BMV capture pad must be set as optical focus. CCD exposure time must be adjusted to the maximum possible contrast of halo boundaries. Hereby, the capture pad should appear as bright as possible.

The visible diameter of the via hole (or clean capture pad), the inner (innermost) and the outer (outermost) appearing halo like boundaries are measured and recorded according FIG. 2. The actual halo values can now be calculated by using following relations.

$$\text{Outer Halo } (\mu m) = (\text{Outermost Diameter } (\mu m) - \text{Diameter of Via Hole } (\mu m))/2 \quad 1.$$

$$\text{Inner Halo } (\mu m) = (\text{Inner Diameter of Halo } (\mu m) - \text{Diameter of Via Hole } (\mu m))/2 \quad 2.$$

Typically, this process is iterated at least 3 times at random test vias to enable minimal statistical statements.

TABLE 4

| | | | halo sizes (in μm): | | | | | | | |
|---|---|---|---|---|---|---|---|---|---|---|
| | | | GX-T31 (μm halo size) | | | | GL102 (μm halo size) | | | |
| | | | Without step (i-c) | | With step (i-c) [300 s] | | Without step (i-c) | | With step (i-c) [300 s] | |
| Sample | Silane | solvent | inner | outer | inner | outer | inner | outer | inner | outer |
| C1 (comparative) | none | | — | 126 | — | 12 | 79 | 142 | 19 | 61 |
| 1 | (VIa) | MeOH | | | | | | | | |
| 2 | (VIa) | DEGBE | | | | | | | | |
| 3 | (VIa) | DEGBE | — | 35 | — | 10 | | | | |

TABLE 4-continued

| halo sizes (in µm): | | | | | | | | | | |
|---|---|---|---|---|---|---|---|---|---|---|
| | | | GX-T31 (µm halo size) | | | | GL102 (µm halo size) | | | |
| | | | Without step (i-c) | | With step (i-c) [300 s] | | Without step (i-c) | | With step (i-c) [300 s] | |
| Sample | Silane | solvent | inner | outer | inner | outer | inner | outer | inner | outer |
| 4 | (VIa) | DEGBE + $H_2O$ (20:80) | — | 62 | — | 12 | | | | |
| 5 | (VIa) | DEGBE + $H_2O$ (20:80) | | | | | | | | |
| 6 | (VIb) | DEGBE | — | 59 | — | 7 | 26 | 71 | 16 | 42 |
| 7 | (VIa) | DEGBE + $H_2O$ (20:80) | | | | | 34 | 110 | 15 | 48 |
| 8 | (VIa) | DEGBE | | | | | 20 | 100 | 20 | 69 |
| 9 | (VIb) | DEGBE | | | | | 29 | 100 | 19 | 39 |
| 10 | (VIb) | DEGBE | | | | | 18 | 72 | 21 | 25 |
| 11 | (VIa) | DEGBE + $H_2O$ (50:50) | | | | | 55 | 150 | 22 | 72 |
| 12 | (VIb) | DEGBE | | | | | | | | |
| 13 | (VIa) | DEGBE + $H_2O$ | | | | | 39 | 150 | 19.8 | 56.4 |

The experiments show that the inventive examples exhibit a good behavior regarding avoidance of wedge void formation, here expressed as halo sizes.

2) Wedge Void Evaluation

In addition, substrates were subjected to Focused Ion Beam (FIB) cuts and subsequent Scanning Electron Microscopy (SEM) measurement. This method allows to analyse the copper adhesion in the vicinity of a blind micro via (BMV), also known as wedge void.

The invention claimed is:

1. A triazine silane compound of formula (I)

(I)

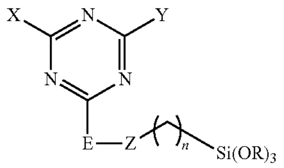

wherein

X and Y are $NH_2$;

E is selected from the group consisting of —S— and —NH—$(CH_2)_m$—NH—;

Z is selected from the group consisting of

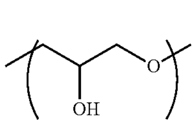 and 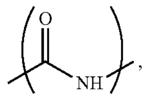, m is an integer in the range from 2 to 12, n is an integer in the range from 1 to 12, is an integer in the range from 2 to 12, R independently denotes $(CH_2—CH_2—O)_p$-T, wherein independently p is 0, 1, 2, 3, or 4, and T denotes H or C1 to C5 alkyl.

2. A triazine silane compound of claim 1, wherein E is —NH—$(CH_2)_m$—NH—, exhibiting a structure of formula (II)

(II)

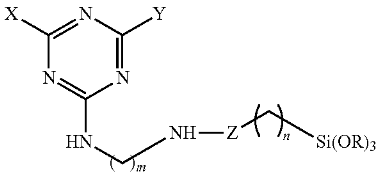

wherein

X and Y $NH_2$;

Z is selected from the group consisting of

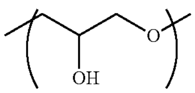 and 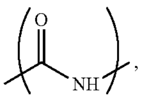, m is an integer in the range from 2 to 12, n is an integer in the range from 1 to 12, is an integer in the range from 2 to 12, R independently denotes $(CH_2—CH_2—O)_p$-T, wherein independently p is 0, 1, 2, 3, or 4, and T denotes H or C1 to C5 alkyl.

3. A mixture comprising (a) one or more than one triazine silane compound according to claim 1, and/or one or more than one triazine silane oligomer of the triazine silane compound, and (b) one or more than one organic solvent.

4. A storage solution comprising (a) one or more than one triazine silane compound according to claim 1, and optionally one or more than one triazine silane oligomer of the triazine silane compound, (b) optionally, water, and (c) one or more than one water miscible organic solvent, with the proviso that, if water is present, the pH is 9 or higher.

5. A working solution having a pH in the range from 2 to 14, the solution comprising (a) one or more than one triazine silane compound according to claim 1, and/or, one or more than one triazine silane oligomer of the triazine silane compound, (b) optionally, water, and (c) one or more than one water miscible organic solvent, wherein in said working solution the total amount of all triazine silane compounds and all triazine silane oligomers together is 5 wt.-% or less, based on the total weight of the working solution.

6. The storage solution according to claim 4, wherein the one or more than one water miscible organic solvent comprises a water-miscible organic solvent selected from the group consisting of C1 to C4 alcohols, ethers, glycol ethers, and mixtures thereof.

7. A synthesis method for a triazine silane compound of formula (II)

(II)

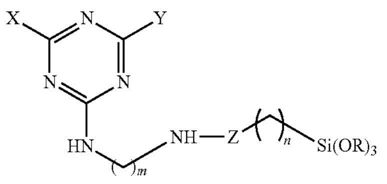

wherein X and Y are independently selected from the group consisting of $NH_2$, $NH(NH_2)$, $NH(CH_2)_oNH_2$, SH, $SCH_3$, and $OCH_3$;

Z is selected from the group consisting of

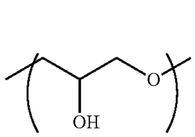 and 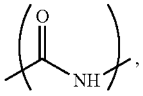, m is an integer in the range from 2 to 12, n is an integer in the range from 1 to 12, is an integer in the range from 2 to 12, R independently denotes $(CH_2—CH_2—O)_p$-T, wherein independently p is 0, 1, 2, 3, or 4, and T denotes H or C1 to C5 alkyl, the synthesis method comprising the steps of (i) providing a compound of formula (III)

(III)

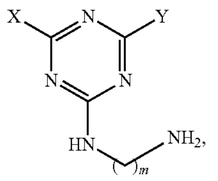

(ii) providing a silane compound selected from the group of (ii-a) a silane compound of formula (IV)

(IV)

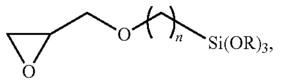

and (ii-b) a silane compound of formula (V)

$$OCN—(CH_2)_n—Si(OR)_3, \quad (V)$$

wherein in formula (IV) or (V)

R denotes $(CH_2—CH_2—O)_p$-T, wherein independently p is 0, 1, 2, 3, or 4, and

T denotes C1 to C5 alkyl, and n is an integer in the range from 1 to 12, reacting in a solvent said intermediate of formula (III) with said silane compound such that above defined compound of formula (II) results, and (iv) optionally hydrolyzing the compound of formula (II) obtained in step (ii such that at least one of R is $(CH_2—CH_2—O)_m$—Z with m=zero and Z=H.

8. A method for increasing adhesion strength between a surface of a metal, a metal alloy or a metal oxide and a surface of an organic material comprising the following steps in this order:

(i) providing a substrate, comprising the metal, metal alloy or metal oxide on at least one side of the substrate, (ii) contacting at least one section of said metal, metal alloy or metal oxide with A) a triazine silane compound of formula (II)

formula (I)

(I)

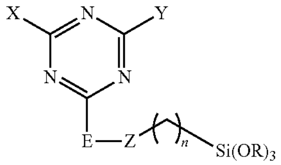

wherein

X and Y are $NH_2$;

E is selected from the group consisting of —S— and —NH—$(CH_2)_m$—NH—;

Z is selected from the group consisting of

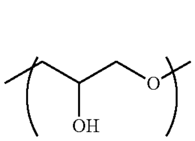 and 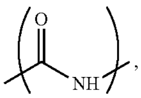, m is an integer in the range from 2 to 12, n is an integer in the range from 1 to 12, is an integer in the range from 2 to 12, R independently denotes $(CH_2—CH_2—O)_p$—Z, wherein independently p is 0, 1, 2, 3, or 4, and T denotes H or C1 to C5 alkyl and/or B) a triazine silane oligomer obtained by reacting the triazine silane compounds of formula (II) with each other in the presence of water such that the triazine silane oligomer comprises at least one silicon-oxygen-silicon moiety, and (iii) applying the organic material such that the at least one section of the metal, metal alloy or metal oxide contacted with the triazine silane compound and/or the triazine silane oligomer during step (ii) is in contact with the applied organic material.

9. The method according to claim 8, wherein the solution further comprises one or more than one water miscible organic solvent.

10. The method according to claim 9, wherein the one or more than one water miscible organic solvent comprises a water-miscible organic solvent selected from the group consisting of C1 to C4 alcohols, ethers, glycol ethers, and mixtures thereof.

11. The method according to claim 9, wherein the total amount of the triazine silane compounds and the triazine silane oligomers together is 5 wt.-% or less, based on the total weight of the solution.

12. The method according to claim 9, wherein the solution has a pH in the range from 2 to 14.

* * * * *